US008680294B2

(12) United States Patent
Traverse et al.

(10) Patent No.: US 8,680,294 B2
(45) Date of Patent: Mar. 25, 2014

(54) ENANTIO- AND STEREO SPECIFIC SYNTHESIS OF β-AMINO-α-HYDROXY AMIDES

(75) Inventors: John Traverse, Roselle Park, NJ (US); William M. Leong, Westfield, NJ (US); Steven P. Miller, Monroe Township, NJ (US); Jennifer Albaneze-Walker, Westfield, NJ (US); Thomas J. Hunter, Middleton, WI (US); Lijun Wang, Dayton, NJ (US); Hongbiao Liao, Bridgewater, NJ (US); Ashok Arasappan, Bridgewater, NJ (US); Scott T. Trzaska, Raritan, NJ (US); Randi M. Smith, Burlingame, CA (US); Azzeddine Lekhal, Highland Park, NJ (US); Stephane L. Bogen, Somerset, NJ (US); Jianshe Kong, Franklin Park, NJ (US); Frank Bennett, Cranford, NJ (US); F. George Njoroge, Carmel, IN (US); Marc Poirier, Stewartsville, NJ (US); Shen-Chun Kuo, Union, NJ (US); Yonggang Chen, Westfield, NJ (US); Kenneth S. Matthews, San Francisco, CA (US); Patrice Demonchaux, Mitterrand (FR); Amadeo Ferreira, Maiaux (FR)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/387,619

(22) PCT Filed: Jul. 27, 2010

(86) PCT No.: PCT/US2010/043356
§ 371 (c)(1),
(2), (4) Date: Mar. 30, 2012

(87) PCT Pub. No.: WO2011/014494
PCT Pub. Date: Feb. 3, 2011

(65) Prior Publication Data
US 2012/0178942 A1 Jul. 12, 2012

Related U.S. Application Data

(60) Provisional application No. 61/229,613, filed on Jul. 29, 2009, provisional application No. 61/229,648, filed on Jul. 29, 2009, provisional application No. 61/229,636, filed on Jul. 29, 2009, provisional application No. 61/229,652, filed on Jul. 29, 2009, provisional application No. 61/229,618, filed on Jul. 29, 2009.

(51) Int. Cl.
*C07D 207/06* (2006.01)
(52) U.S. Cl.
USPC ........................................ 548/452

(58) Field of Classification Search
None
See application file for complete search history.

(56) References Cited

U.S. PATENT DOCUMENTS

| 7,309,717 | B2 | 12/2007 | Park et al. |
| 7,612,237 | B2 | 11/2009 | Knaup |
| 8,067,379 | B2 | 11/2011 | Bennett et al. |
| 2007/0042968 | A1 | 2/2007 | Bennett et al. |

FOREIGN PATENT DOCUMENTS

| EP | 1876168 A1 | 1/2008 |
| EP | 2039689 A1 | 3/2009 |

OTHER PUBLICATIONS

Beevers et al, 'Solution and solid-Phase synthesis of potent inhibitors of hepatitis C Virus NS3 proteinase', Bioorg. Med. Chem. Lett., 2002, 12, 641-643.
Beight et al, 'Synthesis of constrained thiorphan analogs as inhibitors of neutral endopeftidase' Bioorg. Med. Chem. Lett., 1996, 6, 2053-2058.
Berge et al, 'Pharmaceutical salts', Journal of Pharmaceutical Sciences (1977) 66(1): 1-19.
Concellon, et al, 'Direct reaction of dibromoacetic acid with aldehydes promoted by samarium diiodide: an easy, efficient, and rapid synthesis of (E)-alpha,beta-unsaturated carboxylic acids with total stereoselectivity', J. Org. Chem., 2006, 71, 1728-1731.
Gould, P., 'Salt selection for basic drugs', International J. of Pharmaceutics (1986) 33: 201-217.
Arasappan, et al., "Discovery of Narlaprevir: a potent, second generation HCV NS3 serine protease inhibitor", ACS Medicinal Chemistry Letters, vol. 1, pp. 64-69 (2010).

(Continued)

*Primary Examiner* — Nyeemah A Grazier
(74) *Attorney, Agent, or Firm* — Sheldon O. Heber; Julie M. Lake

(57) ABSTRACT

Processes useful for the preparation of a Compound of Formula I: Formula (I). Intermediates useful for the preparation of the compound of Formula I, and processes useful for preparing said intermediates are disclosed.

Formula (I)

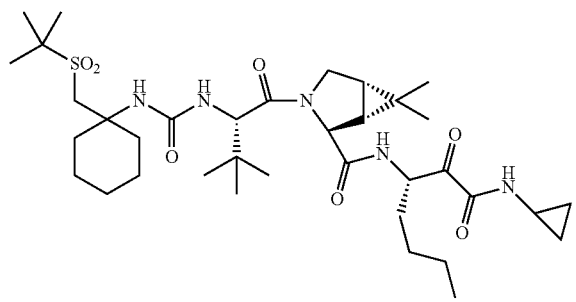

7 Claims, No Drawings

(56) References Cited

OTHER PUBLICATIONS

Bogen, et al., "Discovery of potent sulfonamide P4-capped ketoamide second generation inhibitors of hepatitis C virus NS3 serine protease with favorable pharmacokinetic profiles in preclinical", Bioorganic & Medicinal Chemistry, vol. 18, pp. 1854-1865 (2010).

Venkatraman, et al., "Potent ketoamide inhibitors of HCV NS3 protease derived from quaternized P1 groups", Bioorganic and Medicinal Chemistry Letters, vol. 20, pp. 2151-2155 (2010).

Viso, et al., "Alfa, Beta-Diamino acids: biological significance and synthetic approaches", Chemical Reviews, vol. 105, pp. 3167-3196 (2005).

ENANTIO- AND STEREO SPECIFIC SYNTHESIS OF β-AMINO-α-HYDROXY AMIDES

CROSS-REFERENCE TO RELATED APPLICATIONS

This application is a National Stage application of International Patent Application No. PCT/US2010/043356, filed Jul. 27, 2010, which claims priority to U.S. Provisional Application Nos. 61/229,613 filed on Jul. 29, 2009; 61/229,648 filed on Jul. 29, 2009; 61/229,636 filed on Jul. 29, 2009; 61/229,652 filed on Jul. 29, 2009 and 61/229,618 filed on Jul. 29, 2009.

FIELD OF THE INVENTION

The present invention relates to a process for the preparation of the compound of Formula I which has been shown to have activity as an HCV protease inhibitor. The present invention relates also to a process for the preparation of intermediate compounds useful in preparing the compound of Formula I, referred to herein also as (1R,5S)—N-[1(S)-[2-(cyclopropylamino)-1,2-dioxoethyl]pentyl]-3-[2(S)-[[[[1-[[1,1-dimethylethyl)sulfonyl]methyl]cyclohexyl]amino]carbonyl]amino]-3,3-dimethyl-1-oxobutyl]-6,6-dimethyl-3-azabicyclo[3.1.0]hexane-2(S)-carboxamide.

BACKGROUND

Identification of any publication in this section or any section of this application is not an admission that such publication is prior art to the present invention.

The compound of Formula I is generically and specifically disclosed in Published U.S. Patent No. 2007/0042968, published Feb. 22, 2007 (the '968 publication), now U.S. Pat. No. 8,067,379, incorporated herein by reference.

Processes suitable for making the compound of Formula I are generally described in the '968 publication. In particular, the '968 publication discusses preparing a sulfone carbamate compound, for example, the compound of Formula 837 comprising a cyclic sulfone substituent (paragraphs [0395] through [0403]). The following reaction scheme describes the procedure:

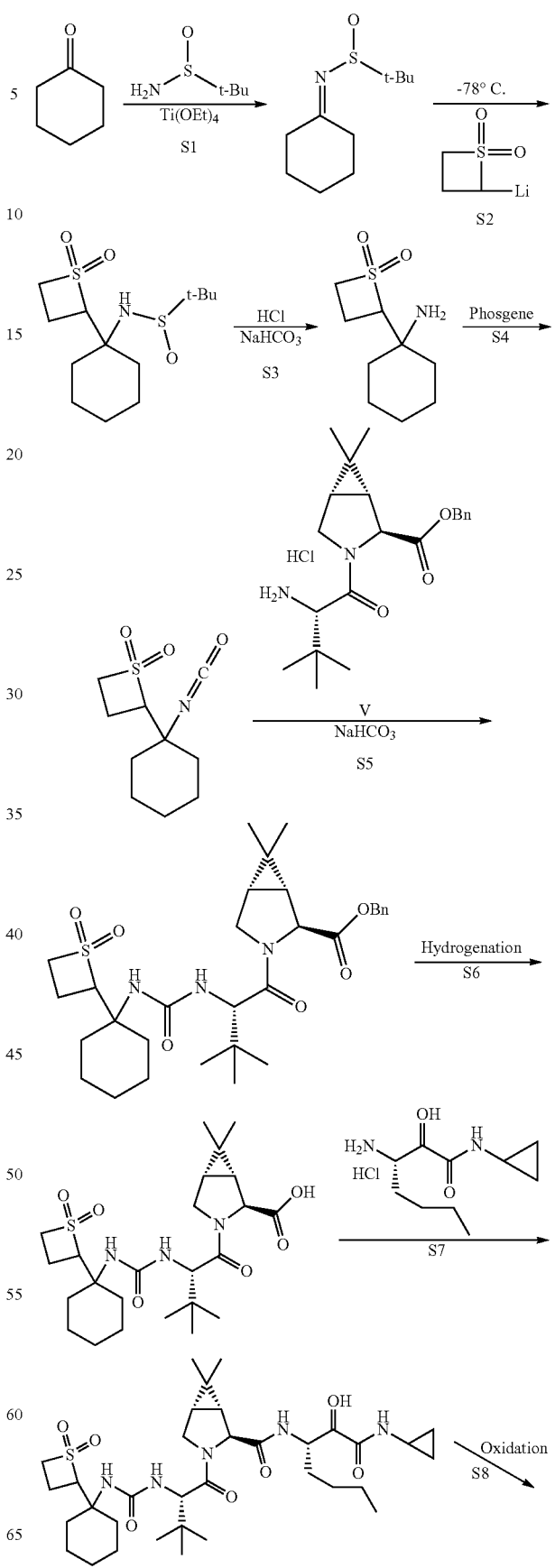

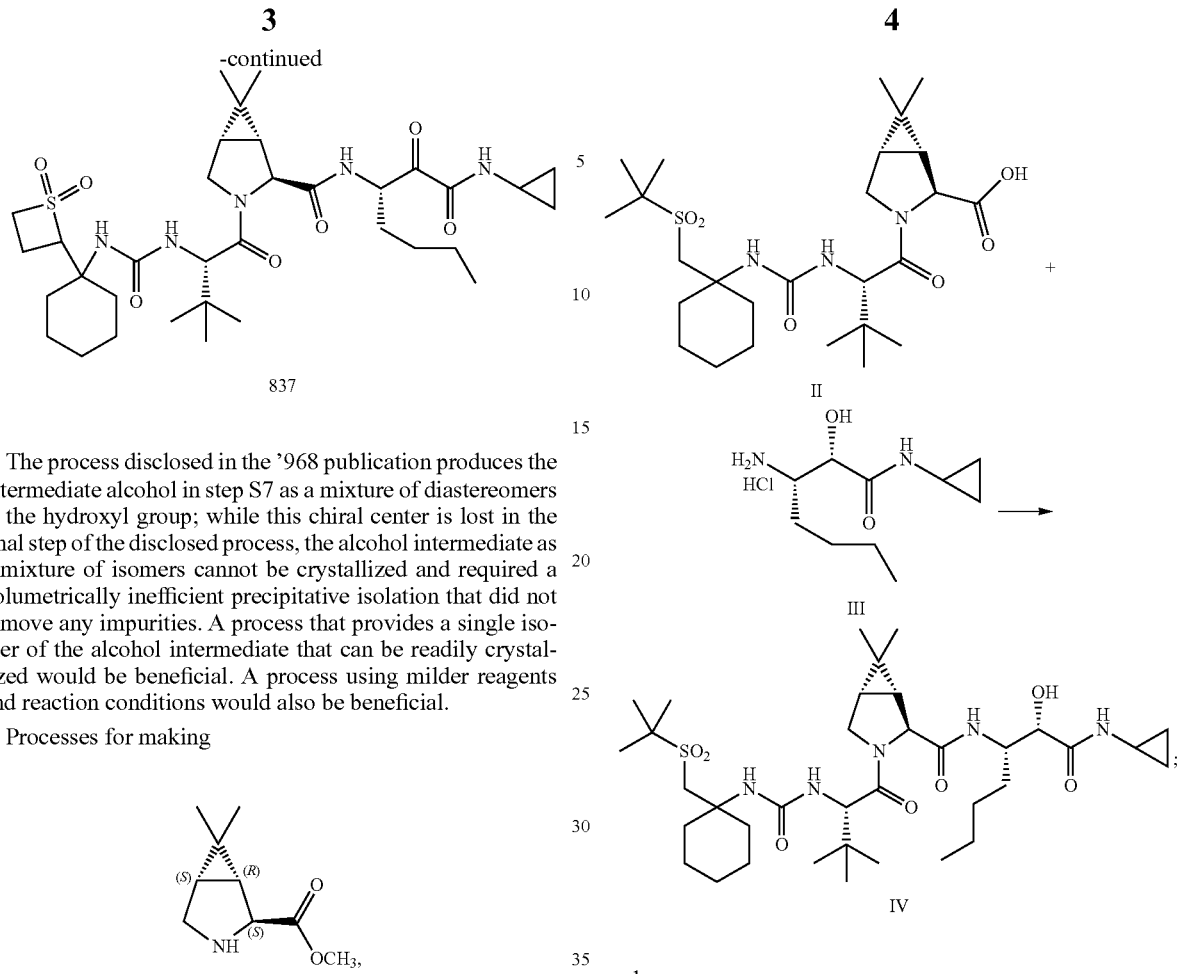

The process disclosed in the '968 publication produces the intermediate alcohol in step S7 as a mixture of diastereomers at the hydroxyl group; while this chiral center is lost in the final step of the disclosed process, the alcohol intermediate as a mixture of isomers cannot be crystallized and required a volumetrically inefficient precipitative isolation that did not remove any impurities. A process that provides a single isomer of the alcohol intermediate that can be readily crystallized would be beneficial. A process using milder reagents and reaction conditions would also be beneficial.

Processes for making

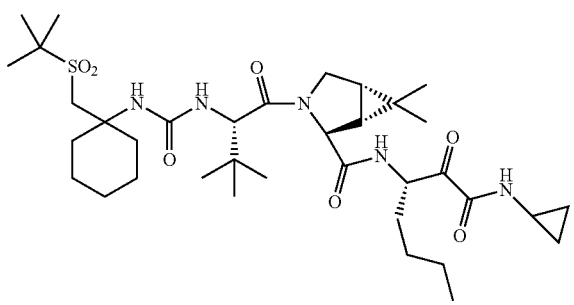 [SMILES: CCCC[C@H](NC(=O)[C@@H]1[C@@H]2[C@H](CN1C(=O)[C@@H](NC(=O)NC1(CS(=O)(=O)C(C)(C)C)CCCCC1)C(C)(C)C)C2(C)C)C(=O)C(=O)NC1CC1]

or a salt thereof, an intermediate in the process of the present invention, are disclosed in the '968 publication and in U.S. Pat. No. 7,309,717, incorporated herein by reference.

SUMMARY OF THE INVENTION

In one aspect, the present invention is a process (Process 1) for preparing the compound of Formula I

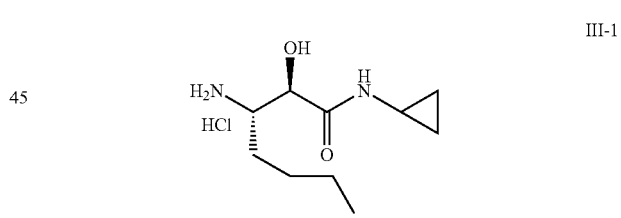

comprising:

1) coupling a bicyclo intermediate of Formula II with an amine intermediate of Formula III in the presence of coupling reagents to obtain the intermediate alcohol of Formula IV:

and 2) oxidizing the intermediate of Formula IV.

Alternatively, Process 1 can employ the diastereomer of compound III, i.e., compound III-1 to obtain the corresponding diastereomer of compound IV-1:

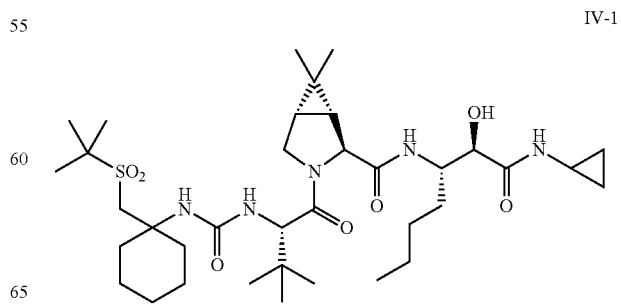

In another alternative, Process 1 can employ salts of the compound of Formula III or Formula III-1 other than the HCl salt.

In other aspects of the invention, processes and intermediates for preparing the compounds of Formula II and Formula III are disclosed as follows:

Process 2:

A process for preparing a compound of Formula V (the ester of Formula II, which is converted to the acid of Formula II by methods known in the art)

V wherein $R^1$ is alkyl, aryl, alkenyl, alkynyl or benzyl, comprising:

1) coupling the acid of Formula VI with the secondary amine of Formula VII, wherein $R^1$ is as defined above, in a water soluble solvent in the presence of coupling agents:

VI + VII → V;

2) adding water to the reaction mixture of step 1 to obtain V as a crystalline hydrate;

3) adding the hydrate of step 2 to an organic solvent, reducing the concentration of water; and 4) adding a non-aqueous antisolvent to crystallize anhydrous V.

Process 3:

A process for preparing the intermediate compound of Formula III

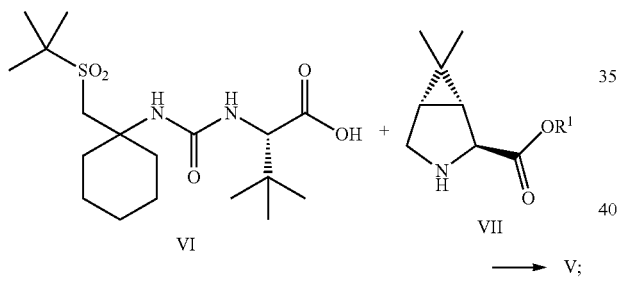

III comprising:

1) condensing valeraldehyde and malonic acid to obtain compound IIIB:

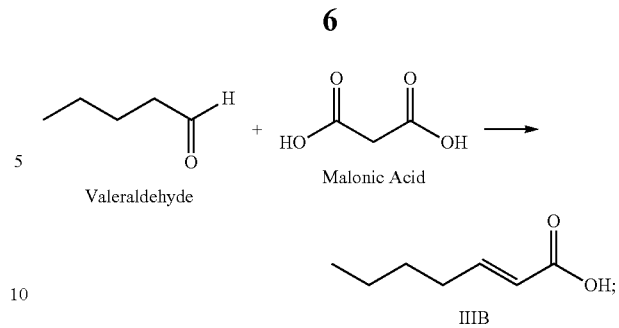

IIIB 2) treating IIIB with 2-methylpropene and an acid to obtain ester IIIC:

IIIB + → IIIC 3) reacting ester IIIC with (S)—N-(−)-benzyl-α-methyl-benzylamine, lithium amide, followed by (1S)-(+)-(10-camphorsulfonyl)-oxaziridine, to obtain the β-amino-α-hydroxy ester IIID:

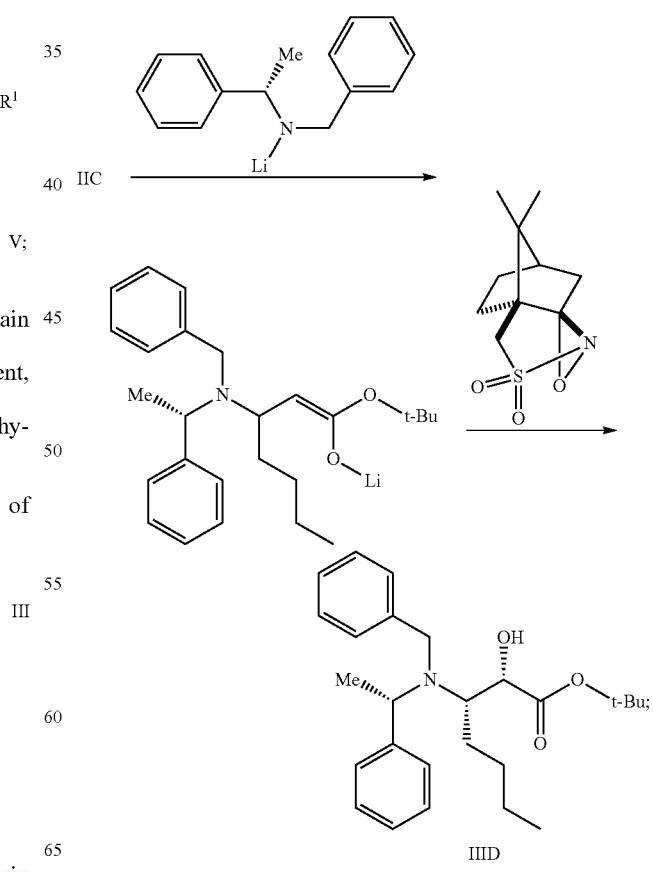

IIID alternatively, IIID is prepared by treating IIID-1 (the deoxy compound) with a lithium amide, followed by treatment with by (1S)-(+)-(10-camphorsulfonyl)-oxaziridine:

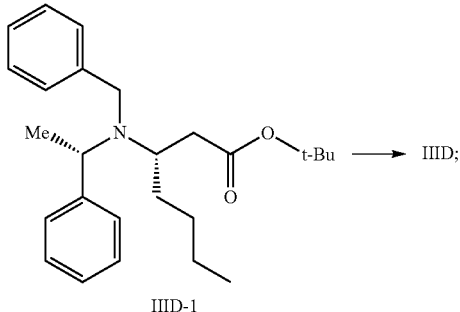

4) converting the ester IIID to the free acid by treating with an acid, then coupling the free acid with cyclopropylamine in the presence of a dehydrating agent to obtain the amide IIIE:

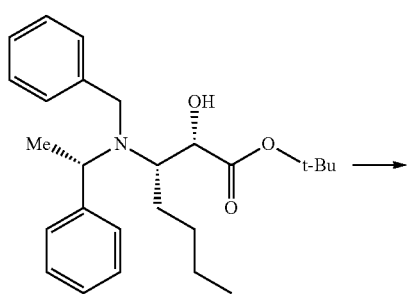

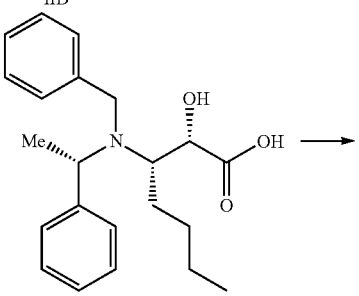

and 5) removing the benzyl protecting groups to obtain amine IIIF, and treating the free amine with HCl to obtain the salt:

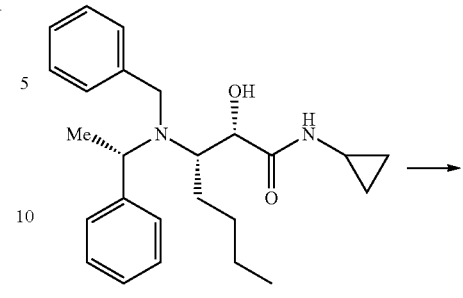

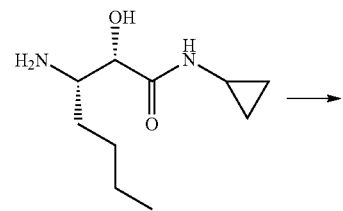

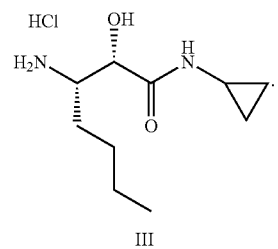

Alternatively, using the appropriate reagents, a procedure similar to Process 3 can be used to prepare the compound of Formula III-1 and its corresponding free amine, IIIF-1:

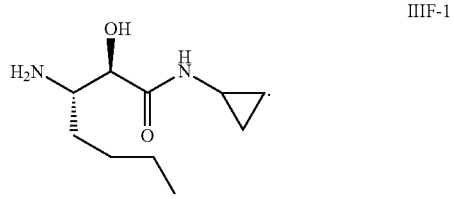

In another alternative, in step 5, an acid other than HCl can be used to prepare a salt of IIIF or IIIF-1

Process 4:

A process for preparing a compound of Formula IIIF comprising opening the ring in the lactam IIIG to obtain amino acid IIIH, coupling IIIH with cyclopropylamine, and deprotecting:

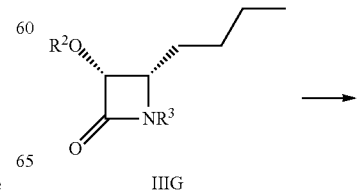

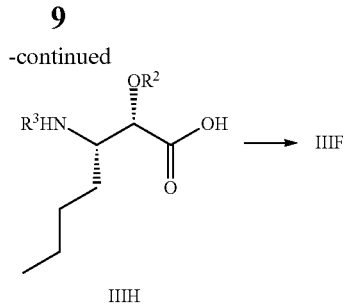

wherein

R² is H, alkyl, aryl, alkenyl, alkynyl, benzyl, —Si(R⁴)₃, —C(O)R⁵, —C(O)OR¹, —C(O)SR¹, —C(O)N(R⁵)₂, —C(S)R⁵, —C(S)OR¹, —C(S)SR¹, —C(S)N(R⁵)₂, —C(NR⁵)R⁵, —C(NR⁵)OR¹, —C(NR⁵)SR¹, —C(NR⁵)N(R⁵)₂, —SOR¹, —SO₂R¹, —SO₃R¹, or —PO(OR¹)₂;

R³ is H, alkyl, aryl, alkenyl, alkynyl, benzyl, —C(O)R⁵ or —C(O)OR¹

R¹ is independently selected from the group consisting of alkyl, aryl, alkenyl, alkynyl and benzyl;

R⁴ is independently selected from the group consisting of alkyl, aryl and alkoxy; and R⁵ is independently selected from the group consisting of H, alkyl, aryl, alkenyl, alkynyl and benzyl.

Process 5:

A process for preparing a compound of Formula IIIF comprising reducing the enamine III-I by asymmetric hydrogenation, converting IIIJ to the carboxylic acid IIIH-1, coupling with cyclopropylamine, and deprotecting:

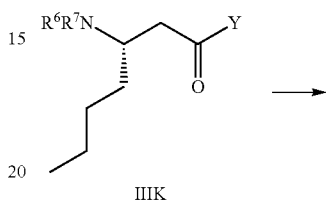

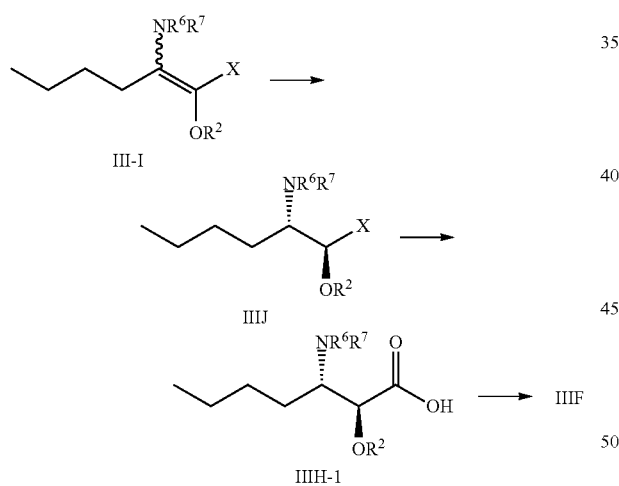

wherein

R² is H, alkyl, aryl, alkenyl, alkynyl, benzyl, —Si(R⁴)₃, —C(O)R⁵, —C(O)OR¹, —C(O)SR¹, —C(O)N(R⁵)₂, —C(S)R⁵, —C(S)OR¹, —C(S)SR¹, —C(S)N(R⁵)₂, —C(NR⁵)R⁵, —C(NR⁵)OR¹, —C(NR⁵)SR¹, —C(NR⁵)N(R⁵)₂, —SOR¹, —SO₂R¹, —SO₃R¹, or —PO(OR¹)₂;

R⁶ and R⁷ are independently selected from the group consisting of H, alkyl, aryl, alkenyl, alkynyl, benzyl, —C(O)R⁵, —C(O)OR¹, —C(O)SR¹, —C(O)N(R⁵)₂, —C(S)R⁵, —C(S)OR¹, —C(S)SR¹, —C(S)N(R⁵)₂, —C(NR⁵)R⁵, —C(NR⁵)OR¹, —C(NR⁵)SR¹, —C(NR⁵)N(R⁵)₂, —SOR¹, —SO₂R¹, —SO₃R¹, and —PO(OR¹)₂;

X is —C(O)R⁵, —CO₂R⁵, —C(O)N(R⁵)₂, —CN, —C(O)SR⁵, —CH₂OH, —CH=CH₂ or —C≡CH;

R¹ is independently selected from the group consisting of alkyl, aryl, alkenyl, alkynyl and benzyl;

R⁴ is independently selected from the group consisting of alkyl, aryl and alkoxy; and R⁵ is independently selected from the group consisting of H, alkyl, aryl, alkenyl, alkynyl and benzyl.

Process 6:

A process for preparing a compound of Formula IIIF comprising hydroxylation of IIIK, to obtain IIIL, converting IIIL to the carboxylic acid IIIH-2, coupling with cyclopropylamine, and deprotecting:

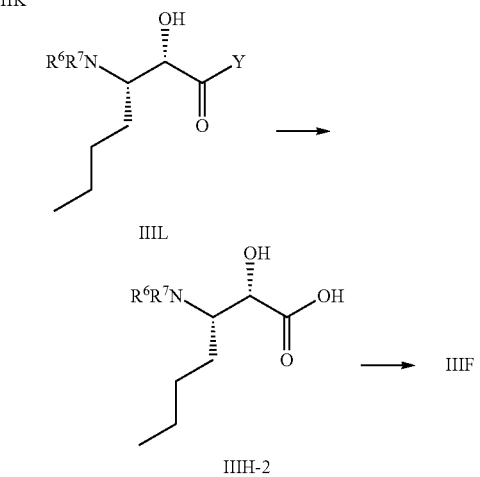

wherein

R⁶ and R⁷ are independently selected from the group consisting of H, alkyl, aryl, alkenyl, alkynyl, benzyl, —C(O)R⁵, —C(O)OR¹, —C(O)SR¹, —C(O)N(R⁵)₂, —C(S)R⁵, —C(S)OR¹, —C(S)SR¹, —C(S)N(R⁵)₂, —C(NR⁵)R⁵, —C(NR⁵)OR¹, —C(NR⁵)SR¹, —C(NR⁵)N(R⁵)₂, —SOR¹, —SO₂R¹, —SO₃R¹, and —PO(OR¹)₂;

Y is —OR⁵, —N(R⁵)₂ or —SR⁵;

R¹ is independently selected from the group consisting of alkyl, aryl, alkenyl, alkynyl and benzyl; and R⁵ is independently selected from the group consisting of H, alkyl, aryl, alkenyl, alkynyl and benzyl.

Process 7:

A process for preparing a compound of Formula IIIF comprising reducing the nitro group of IIIM to obtain the amino acid derivative IIIN, resolving IIIN to obtain IIIO, converting IIIO to the carboxylic acid IIIH-3, coupling with cyclopropylamine, and deprotecting:

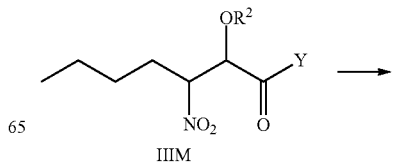

-continued

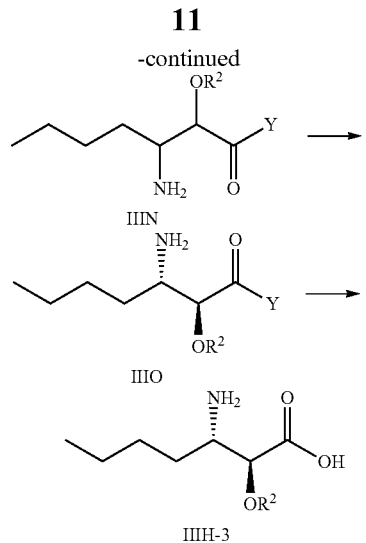

wherein
R² is H, alkyl, aryl, alkenyl, alkynyl, benzyl, —Si(R⁴)₃, —C(O)R⁵, —C(O)OR¹, —C(O)SR¹, —C(O)N(R⁵)₂, —C(S)R⁵, —C(S)OR¹, —C(S)SR¹, —C(S)N(R⁵)₂, —C(NR⁵)R⁵, —C(NR⁵)OR¹, —C(NR⁵)SR¹, —C(NR⁵)N(R⁵)₂, —SOR¹, —SO₂R¹, —SO₃R¹, or —PO(OR¹)₂;
Y is —OR⁵, —N(R⁵)₂ or —SR⁵;
R¹ is independently selected from the group consisting of alkyl, aryl, alkenyl, alkynyl and benzyl;
R⁴ is independently selected from the group consisting of alkyl, aryl and alkoxy; and
R⁵ is independently selected from the group consisting of H, alkyl, aryl, alkenyl, alkynyl and benzyl.

Process 8:

A process for preparing a compound of Formula IIIF comprising reducing the α-keto compound of formula IIIP to obtain the alcohol IIIL, converting IIII to the carboxylic acid IIIH-2, coupling with cyclopropylamine, and deprotecting:

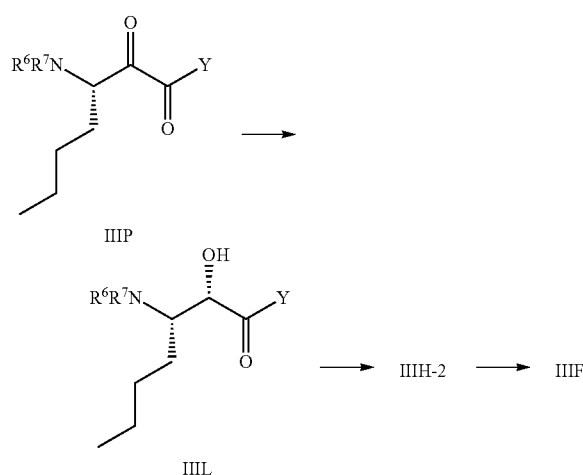

wherein
R⁶ and R⁷ are independently selected from the group consisting of H, alkyl, aryl, alkenyl, alkynyl, benzyl, —C(O)R⁵, —C(O)OR¹, —C(O)SR¹, —C(O)N(R⁵)₂, —C(S)R⁵, —C(S)OR¹, —C(S)SR¹, —C(S)N(R⁵)₂, —C(NR⁵)R⁵, —C(NR⁵)OR¹, —C(NR⁵)SR¹, —C(NR⁵)N(R⁵)₂, —SOR¹, —SO₂R¹, —SO₃R¹, and —PO(OR¹)₂;
Y is —OR⁵, —N(R⁵)₂ or —SR⁵;
R¹ is independently selected from the group consisting of alkyl, aryl, alkenyl, alkynyl and benzyl; and
R⁵ is independently selected from the group consisting of H, alkyl, aryl, alkenyl, alkynyl and benzyl.

Process 9:

A process for preparing a compound of Formula IIIF comprising converting IIIQ to the amine IIIJ through a displacement reaction that inverts the stereochemistry, converting IIIJ to the carboxylic acid IIIH-1, coupling with cyclopropylamine, and deprotecting:

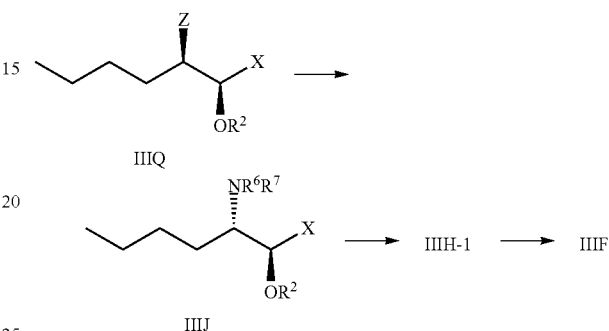

wherein
R² is H, alkyl, aryl, alkenyl, alkynyl, benzyl, —Si(R⁴)₃, —C(O)R⁵, —C(O)OR¹, —C(O)SR¹, —C(O)N(R⁵)₂, —C(S)R⁵, —C(S)OR¹, —C(S)SR¹, —C(S)N(R⁵)₂, —C(NR⁵)R⁵, —C(NR⁵)OR¹, —C(NR⁵)SR¹, —C(NR⁵)N(R⁵)₂, —SOR¹, —SO₂R¹, —SO₃R¹, or —PO(OR¹)₂;
R⁶ and R⁷ are independently selected from the group consisting of H, alkyl, aryl, alkenyl, alkynyl, benzyl, —C(O)R⁵, —C(O)OR¹, —C(O)SR¹, —C(O)N(R⁵)₂, —C(S)R⁵, —C(S)OR¹, —C(S)SR¹, —C(S)N(R⁵)₂, —C(NR⁵)R⁵, —C(NR⁵)OR¹, —C(NR⁵)SR¹, —C(NR⁵)N(R⁵)₂, —SOR¹, —SO₂R¹, —SO₃R¹, and —PO(OR¹)₂;
X is —C(O)R⁵, —CO₂R⁵, —C(O)N(R⁵)₂, —CN, —C(O)SR⁵, —CH₂OH, —CH=CH₂ or —C≡CH;
R¹ is independently selected from the group consisting of alkyl, aryl, alkenyl, alkynyl and benzyl;
R⁴ is independently selected from the group consisting of alkyl, aryl and alkoxy;
R⁵ is independently selected from the group consisting of H, alkyl, aryl, alkenyl, alkynyl and benzyl; and
Z is a leaving group such as, but not limited to halogen, OMs or OTs.

Process 10:

A process for preparing a compound of Formula IIIF comprising treating an epoxide IIIR with a nitrogen source to open the ring to obtain IIIS, converting IIIS to the carboxylic acid IIIH-4, and coupling with cyclopropylamine:

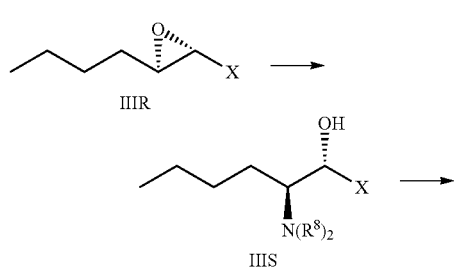

-continued

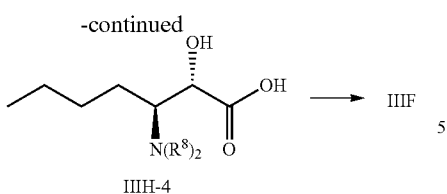

IIIH-4 wherein

R⁵ is independently selected from the group consisting of H, alkyl, aryl, alkenyl, alkynyl, benzyl, —C(O)R⁵ and —C(O)OR¹;

X is —C(O)R⁵, —CO₂R⁵, —C(O)N(R⁵)₂, —CN, —C(O)SR⁵, —CH₂OH, —CH=CH₂ or —C≡CH;

R¹ is independently selected from the group consisting of alkyl, aryl, alkenyl, alkynyl and benzyl; and R⁵ is independently selected from the group consisting of H, alkyl, aryl, alkenyl, alkynyl and benzyl.

Process 11:

A process for preparing a compound of Formula IIIF comprising treating an aziridine IIIT with an oxygen source to open the ring to obtain IIIU, converting IIIU to the carboxylic acid IIIH-5, coupling with cyclopropylamine, and deprotecting:

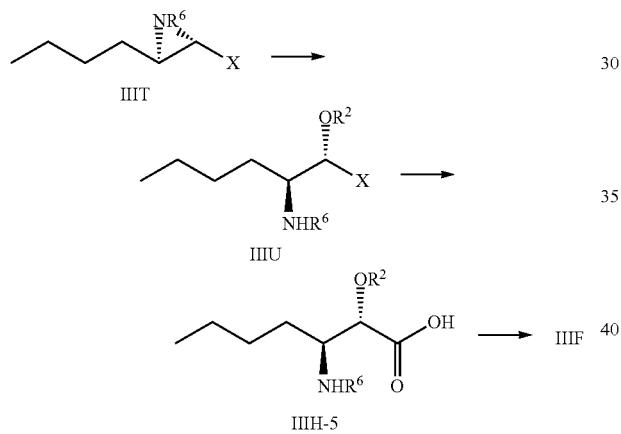

wherein

R² is H, alkyl, aryl, alkenyl, alkynyl, benzyl, —Si(R⁴)₃, —C(O)R⁵, —C(O)OR¹, —C(O)SR¹, —C(O)N(R⁵)₂, —C(S)R⁵, —C(S)OR¹, —C(S)SR¹, —C(S)N(R⁵)₂, —C(NR⁵)R⁵, —C(NR⁵)OR¹, —C(NR⁵)SR¹, —C(NR⁵)N(R⁵)₂, —SOR¹, —SO₂R¹, —SO₃R¹, or —PO(OR¹)₂;

R⁶ H, alkyl, aryl, alkenyl, alkynyl, benzyl, —C(O)R⁵, —C(O)OR¹, —C(O)SR¹, —C(O)N(R⁵)₂, —C(S)R⁵, —C(S)OR¹, —C(S)SR¹, —C(S)N(R⁵)₂, —C(NR⁵)R⁵, —C(NR⁵)OR¹, —C(NR⁵)SR¹, —C(NR⁵)N(R⁵)₂, —SOR¹, —SO₂R¹, —SO₃R¹, or —PO(OR¹)₂;

X is —C(O)R⁵, —CO₂R⁵, —C(O)N(R⁵)₂, —CN, —C(O)SR⁵, —CH₂OH, —CH=CH₂ or —C≡CH;

R¹ is independently selected from the group consisting of alkyl, aryl, alkenyl, alkynyl and benzyl;

R⁴ is independently selected from the group consisting of alkyl, aryl and alkoxy; and R⁵ is independently selected from the group consisting of H, alkyl, aryl, alkenyl, alkynyl and benzyl.

Alternatively, using the appropriate reagents, procedures similar to Processes 4 to 11 can be used to prepare the compound of Formula IIIF-1.

Process 12:

A process for preparing a urea of Formula VI

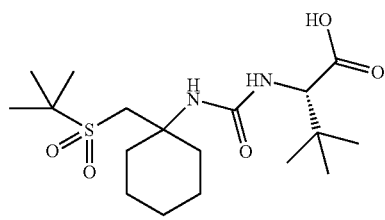

comprising displacing the leaving group of the compound of Formula VIA with an anionic sulfur nucleophile to obtain VIB, converting VIB to the primary amine VIBb (wherein both R⁶ and R⁷ are H), and reacting VIBb with tent-leucine in the presence of phosgene or a phosgene equivalent:

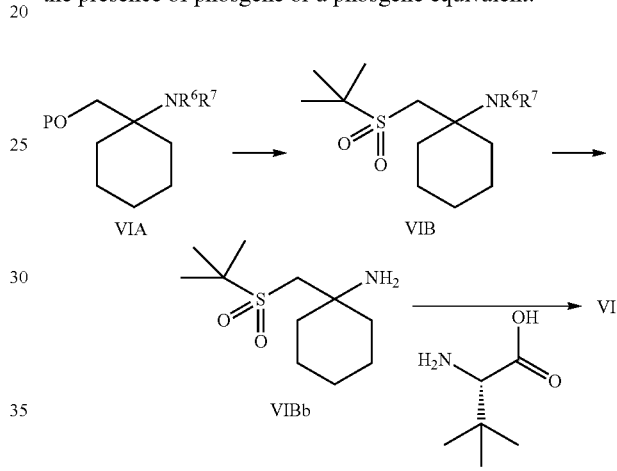

wherein

P is a leaving group;

R⁶ and R⁷ are independently selected from the group consisting of H, alkyl, aryl, alkenyl, alkynyl, benzyl, —C(O)R⁵, —C(O)OR¹, —C(O)SR¹, —C(O)N(R⁵)₂, —C(S)R⁵, —C(S)OR¹, —C(S)SR¹, —C(S)N(R⁵)₂, —C(NR⁵)R⁵, —C(NR⁵)OR¹, —C(NR⁵)SR¹, —C(NR⁵)N(R⁵)₂, —SOR¹, —SO₂R¹, —SO₃R¹, and —PO(OR¹)₂;

R¹ is independently selected from the group consisting of alkyl, aryl, alkenyl, alkynyl and benzyl; and R⁵ is independently selected from the group consisting of H, alkyl, aryl, alkenyl, alkynyl and benzyl.

Process 13:

A process for preparing a urea of Formula VI comprising opening the ring of the aziridine of Formula VIC with a metalated sulfur nucleophile to obtain VIB, converting VIB to the primary amine VIBb, and reacting VIBb with tert-leucine in the presence of phosgene or a phosgene equivalent:

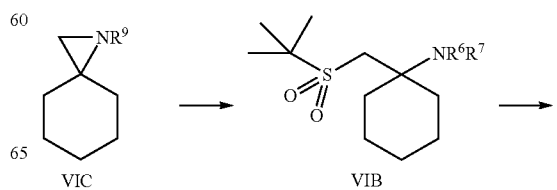

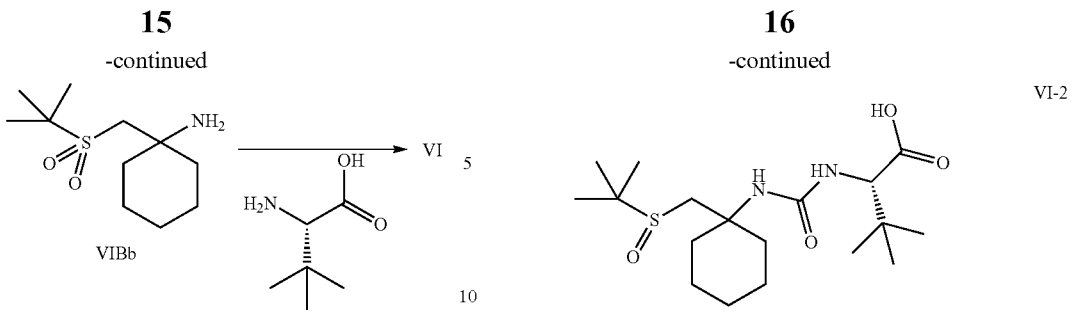

wherein $R^6$, $R^7$ and $R^9$ are independently selected from the group consisting of H, alkyl, aryl, alkenyl, alkynyl, benzyl, —C(O)$R^5$, —C(O)O$R^1$, —C(O)S$R^1$, —C(O)N($R^5$)$_2$, —C(S)$R^5$, —C(S)O$R^1$, —C(S)S$R^1$, —C(S)N($R^5$)$_2$, —C(N$R^5$)$R^5$, —C(N$R^5$)O$R^1$, —C(N$R^5$)S$R^1$, —C(N$R^5$)N($R^5$)$_2$, —SO$R^1$, —SO$_2R^1$, —SO$_3R^1$, and —PO(O$R^1$)$_2$;

$R^1$ is independently selected from the group consisting of alkyl, aryl, alkenyl, alkynyl and benzyl; and $R^5$ is independently selected from the group consisting of H, alkyl, aryl, alkenyl, alkynyl and benzyl.

Process 14:

A process for preparing a urea of Formula VI comprising performing a Curtius rearrangement of the acid of Formula VID (via formation of an acyl azide) to obtain an isocyanate of Formula VIE, and reacting VIE with tert-leucine:

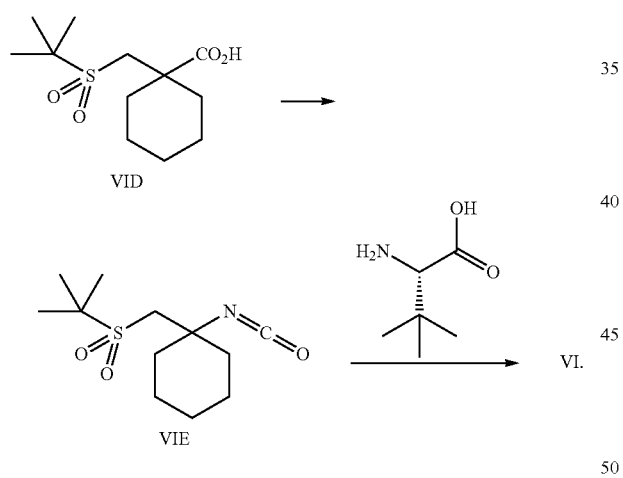

Procedures similar to Processes 12, 13 and 14 can be used to prepare the thio and sulfinyl analogs, VI-1 and VI-2:

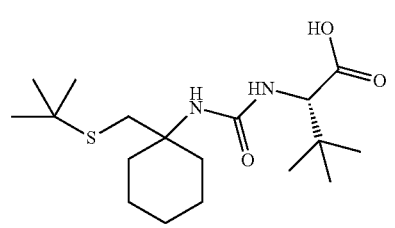

Process 15:

A process for preparing a compound of Formula VIB comprising condensing cyclohexanone with a sulfonyl compound to obtain the unsaturated compound of Formula VIF, then reducing VIF:

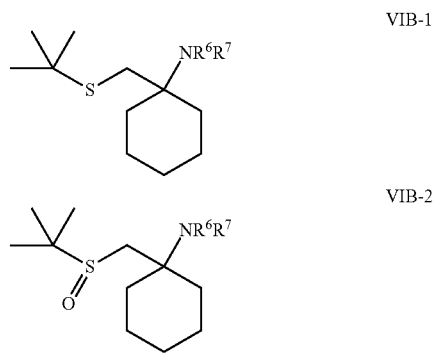

wherein $R^{10}$ is H, —Si($R^4$)$_3$, —C(O)$R^5$, —C(O)O$R^5$, —C(O)N($R^5$)$_2$, $R^4$ is independently selected from the group consisting of alkyl, aryl and alkoxy; and $R^5$ is independently selected from the group consisting of H, alkyl, aryl, alkenyl, alkynyl and benzyl.

A procedure similar to Process 15 can be used to prepare the thio and sulfinyl analogs, VIB-1 and VIB-2:

wherein $R^6$ and $R^7$ are as defined above.

Process 16:

A process for preparing a compound of Formula VID comprising 1) treating a cyclohexane derivative of Formula VIG with a trimethylsilyl compound, followed by alkylation with Pert-butyl chloromethyl sulfide to obtain the compound of Formula VIJ:

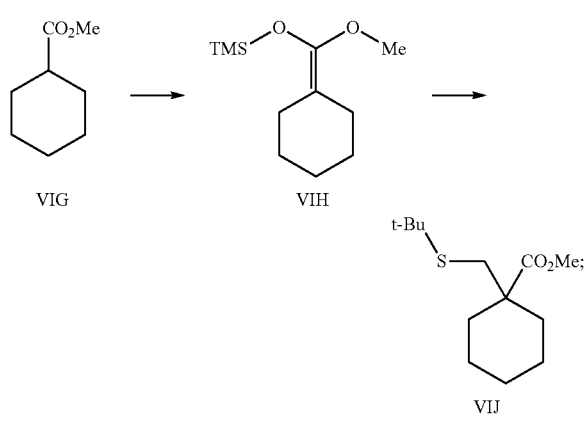

2) hydrolyzing the ester VIJ to the acid VIK:

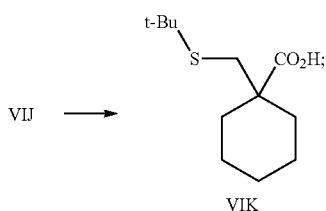

and
3) oxidizing the thioether to the sulfone:

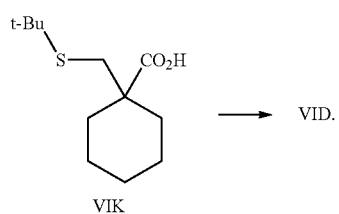

Alternatively, another ester of cyclohexane carboxylic acid, cyclohexane carbonitrile or another carbonyl derivative of cyclohexane can be used in place of the compound VIG, e.g., the carboxylic acid methyl ester can be replaced by —C(O)R⁵, —C(O)OR⁵, —CN, —C(O)N(R⁵)₂ or —C(O)SR⁵, wherein R⁵ is independently H, alkyl, aryl, alkenyl, alkynyl or benzyl.

Process 17:

A process for preparing a compound of Formula VID comprising oxidizing the thioether VIJ to obtain the ester-sulfone VIL, followed by hydrolysis of the ester to obtain the free acid VID:

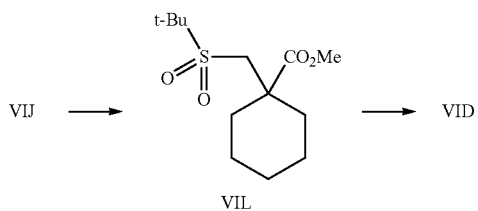

Alternatively the carboxylic acid methyl ester of VIJ can be replaced by —C(O)R⁵, —C(O)OR⁵, —CN, —C(O)N(R⁵)₂ or —C(O)SR⁵, wherein R⁵ is independently H, alkyl, aryl, alkenyl, alkynyl or benzyl.

Process 18:

A process for preparing an isocyanate of formula VIE comprising 1) reacting cyclohexanone with an amine to form an imine VIM, then alkylating VIM with a lithiated sulfone of formula VIN to obtain amino-sulfone VIBa (a compound of formula VIB wherein one of the groups attached to N is H):

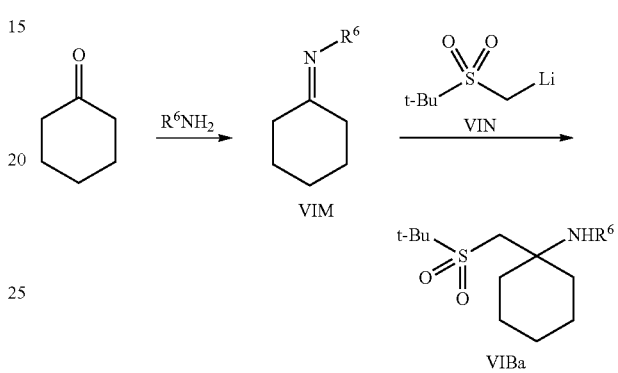

wherein $R^6$ is H, alkyl, aryl, alkenyl, alkynyl, benzyl, —C(O)R⁵, —C(O)OR¹, —C(O)SR¹, —C(O)N(R⁵)₂, —C(S)R⁵, —C(S)OR¹, —C(S)SR¹, —C(S)N(R⁵)₂, —C(NR⁵)R⁵, —C(NR⁵)OR¹, —C(NR⁵)SR¹, —C(NR⁵)N(R⁵)₂, —SOR¹, —SO₂R¹, —SO₃R¹, or —PO(OR¹)₂;

$R^1$ is independently selected from the group consisting of alkyl, aryl, alkenyl, alkynyl and benzyl; and $R^5$ is independently selected from the group consisting of H, alkyl, aryl, alkenyl, alkynyl and benzyl;

and 2) deprotecting the amine VIBa and converting the free amine to the isocyanate:

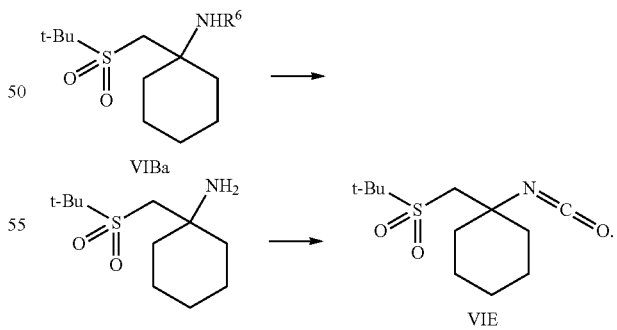

Process 19:

A process for preparing a urea of Formula VI comprising treating an amine of Formula VIBb (a compound of Formula VIB wherein both R groups are H) with phenylchloroformate in the presence of a base to obtain carbamate VIO, and reacting VIO with tent-leucine in the presence of a base:

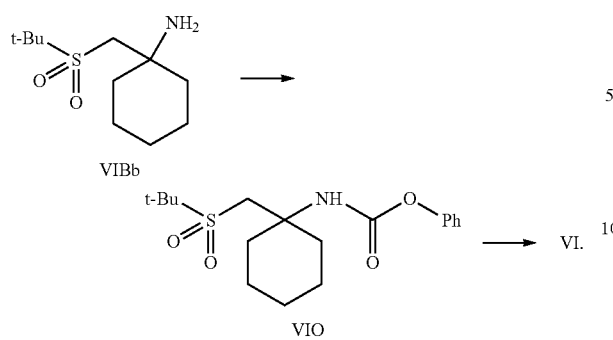

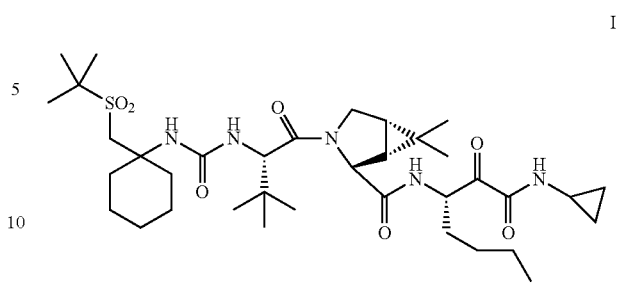

comprising:

1) coupling the acid of Formula VI with the secondary amine of Formula VII-1 (a compound of Formula VII wherein $R^1$ is methyl) in a water soluble solvent in the presence of coupling agents to obtain the ester of Formula Va:

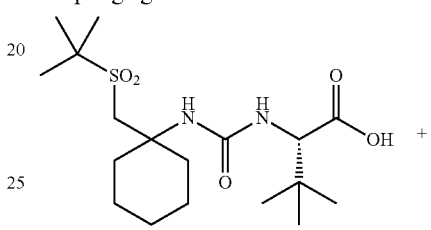

Process 20:

A process for preparing the amine of Formula VIBb comprising condensing cyclohexanone with tert-butyl sulfinamide in the presence of a dehydrating agent to obtain the imine of Formula VIP, treating VIP with VIN to obtain the sulfone-sulfinamide VIQ, and converting VIQ to the free amine:

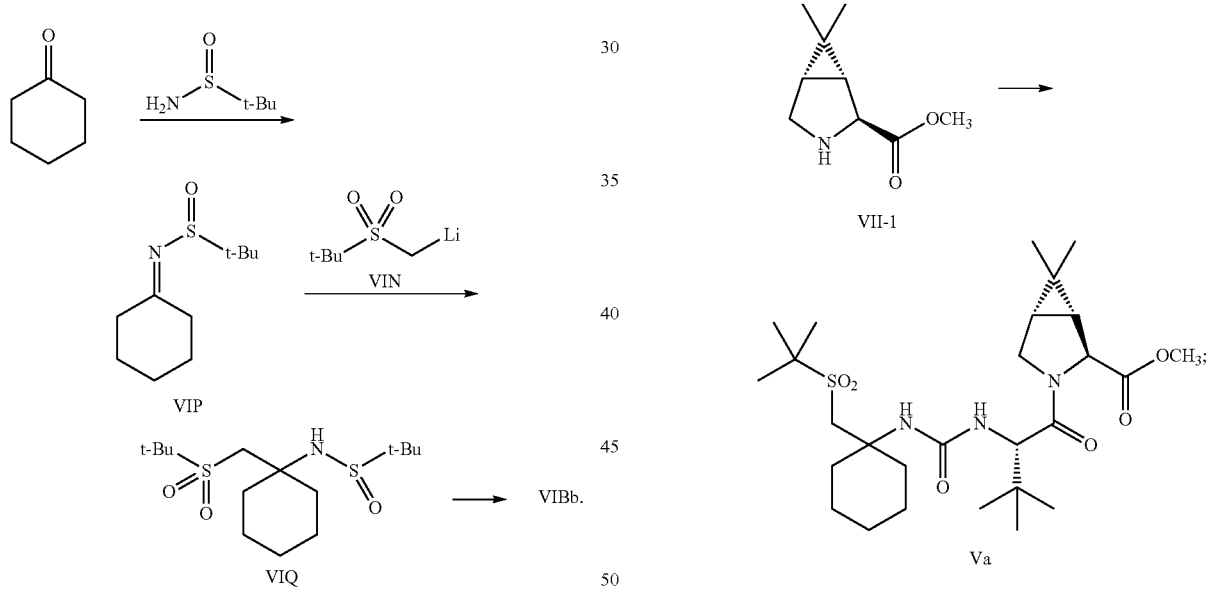

Process 21:

A process for preparing the compound of Formula VIN comprising oxidizing tert-butylthiomethyl ether with hydrogen peroxide and sodium tungstate to obtain VIR, and treating VIR with n-butyl lithium:

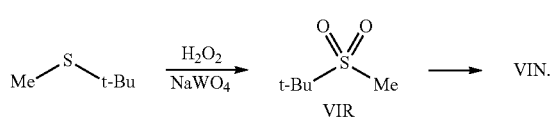

In another aspect, the invention relates to a process (Process 22) for preparing the compound of Formula I 2) converting the ester of Formula Va to the acid of Formula II:

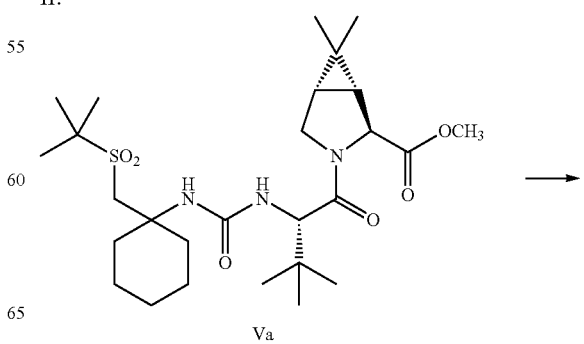

-continued

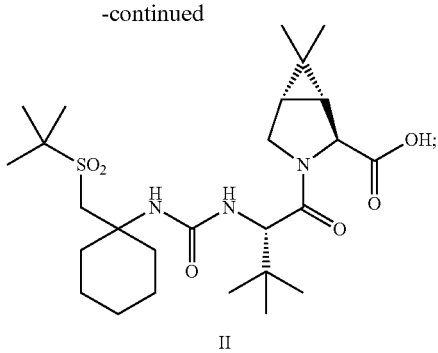

II 3) coupling the acid of Formula II with an amine intermediate of Formula III in the presence of coupling reagents to obtain the intermediate alcohol of Formula IV:

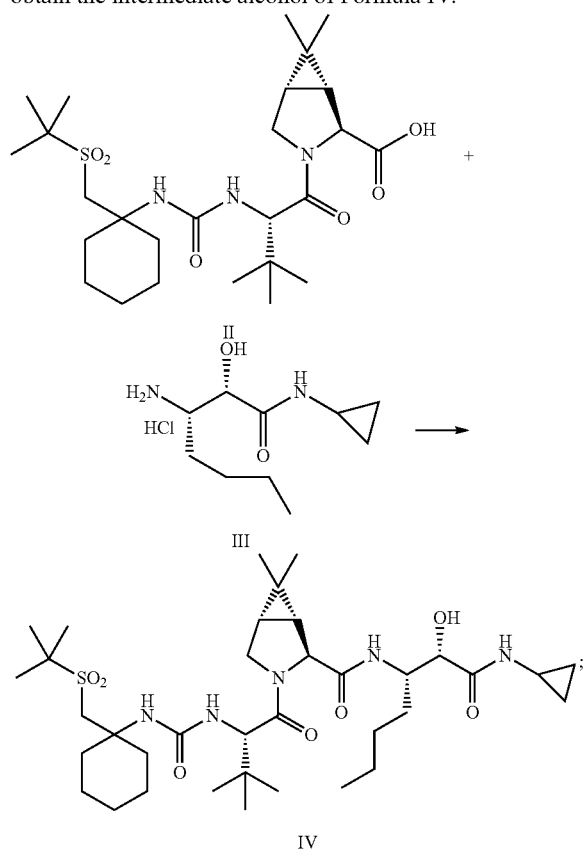

IV and 4) oxidizing the intermediate of Formula IV.

In another aspect, the invention relates to a process (Process 23) for preparing the compound of Formula I

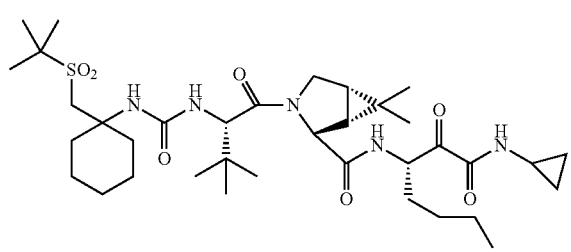

I comprising:

1) reacting a protected amine of Formula VIIA with a cyclopropylamine of Formula III to obtain a compound of Formula VIII

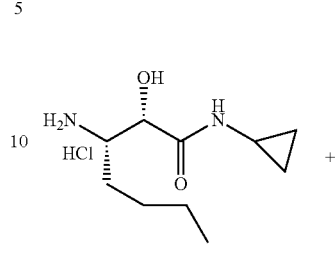

III

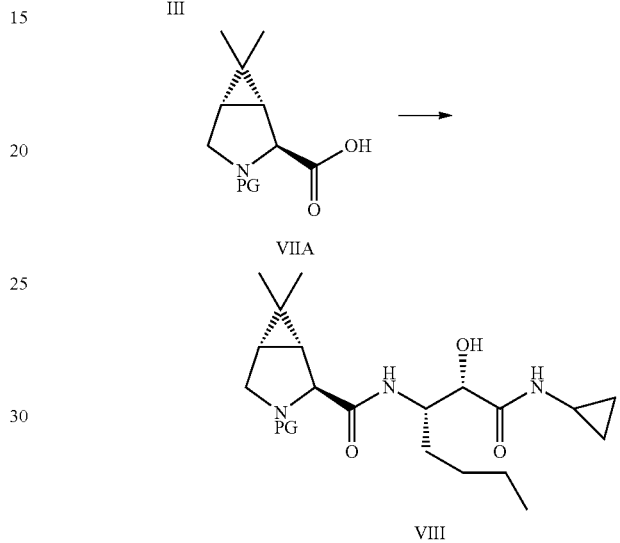

VIIA

VIII wherein PG is a nitrogen protecting group;

2) removing the protecting group from VIII and coupling the resultant free amine of Formula VIIIA with an acid of Formula VI to obtain the alcohol of Formula IV:

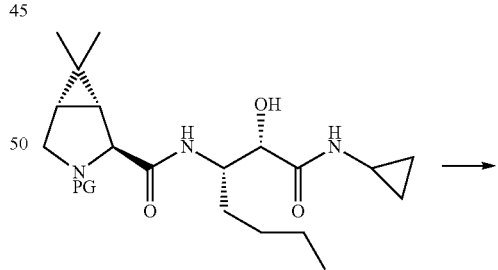

VIII

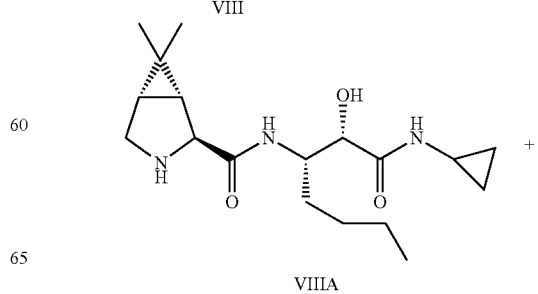

VIIIA

-continued

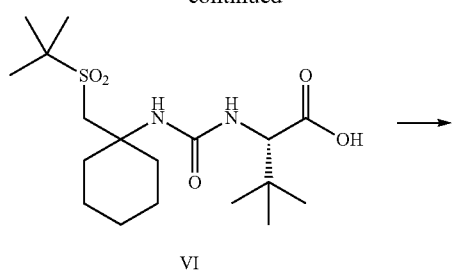

VI

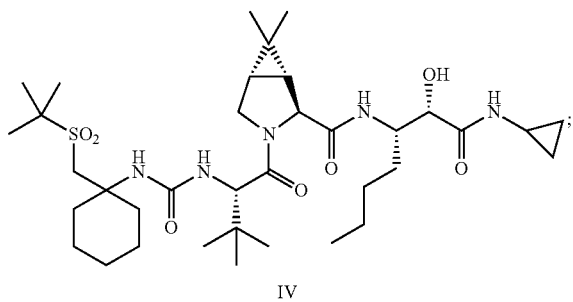

IV and 3) oxidizing the alcohol of Formula IV.

In another aspect, the invention relates to a process (Process 24) for preparing a compound of Formula VI

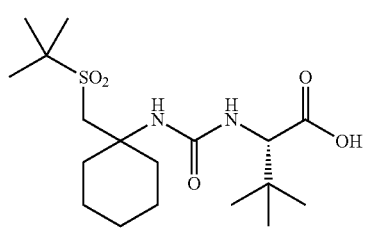

VI comprising:

1) reacting an imine of Formula VIP with the sulfone of Formula VIN to obtain the sulfone-sulfinamide of Formula VIQ, then converting VIQ to the primary amine VIBb:

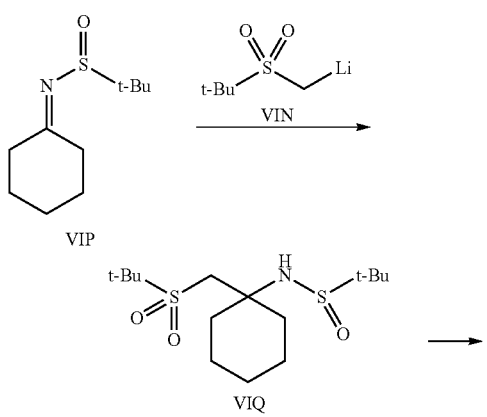

-continued

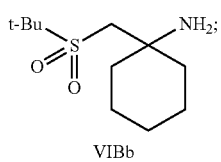

VIBb 2) reacting VIBb with phenylchloroformate in the presence of a base to obtain the carbamate of Formula VIO

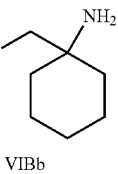

VIBb

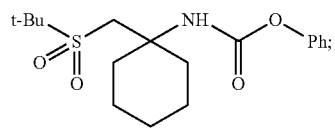

VIO and 3) reacting VIO with Pert-leucine.

In another aspect, the invention relates to a process (Process 25) for preparing the compound of Formula IV

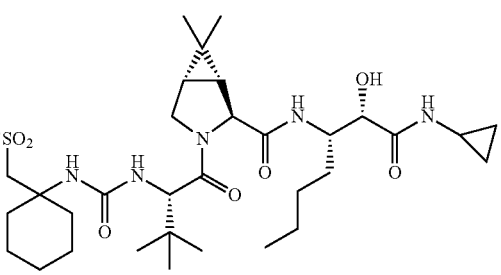

IV comprising:

1) coupling the acid of Formula IX wherein $R^1$ is as defined above with an amine of Formula III to obtain the compound of Formula X

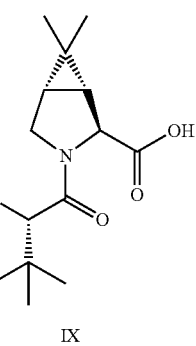

IX

-continued
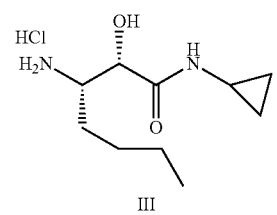
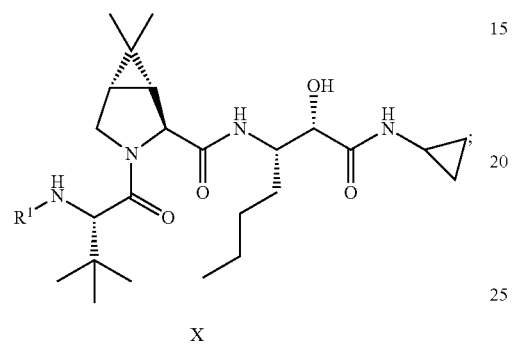
2) deprotecting the amine of Formula X to obtain the compound of Formula XI:
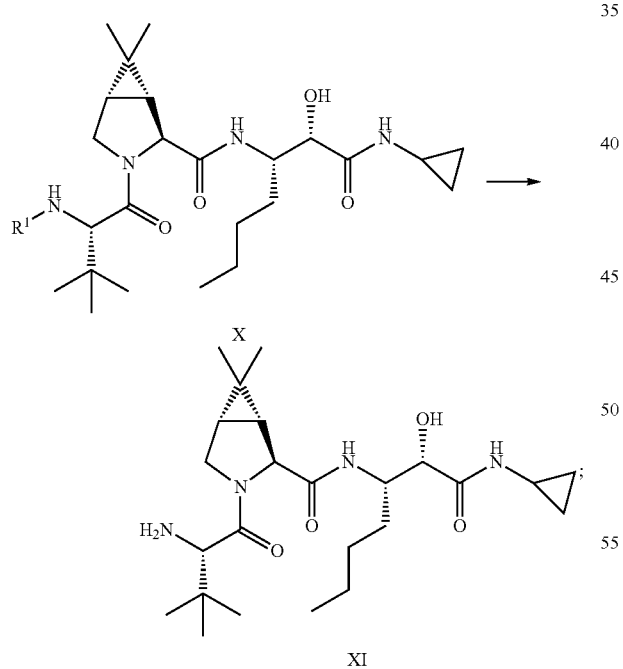
and
3) reacting the amine of Formula XI with the isocyanate of Formula VIE
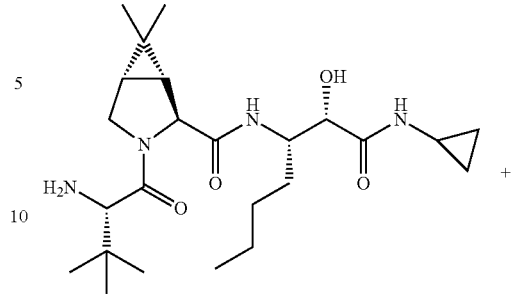
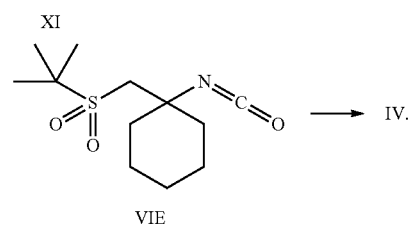
In another aspect, the invention relates to the following novel intermediates:
(II)
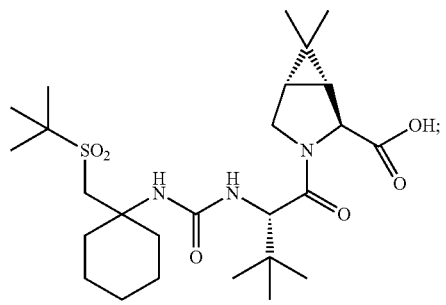
(III)
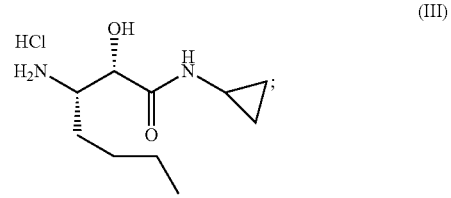
(III-1)
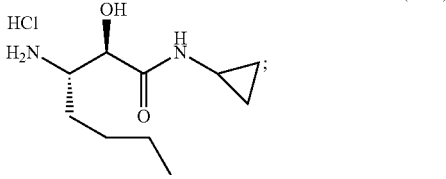
(IIIF)
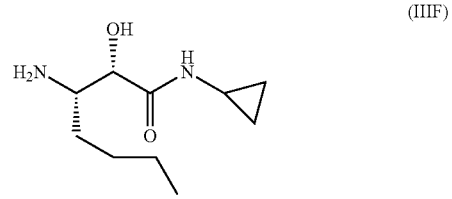

or a salt thereof;

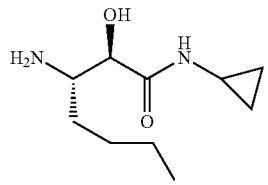

or a salt thereof;

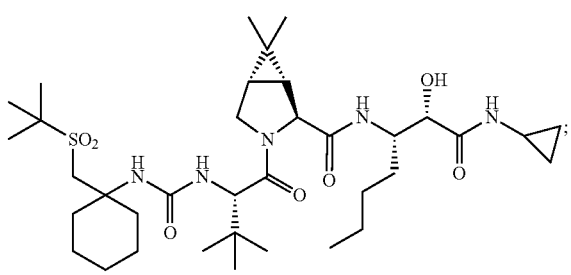

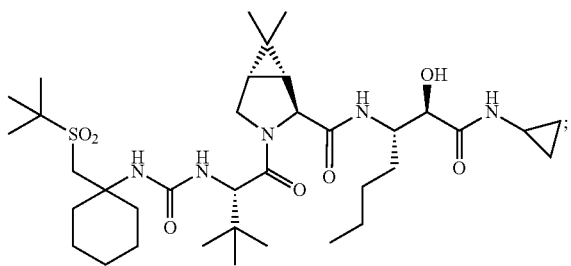

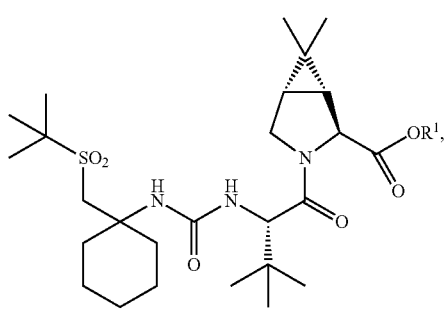

wherein R¹ is alkyl, aryl, alkenyl, alkynyl or benzyl, or a hydrated or anhydrous polymorph thereof;

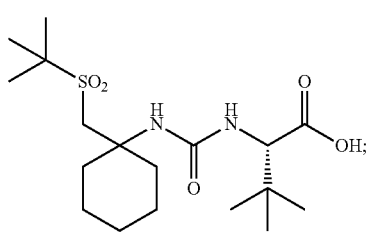

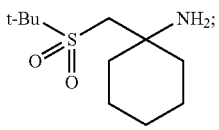

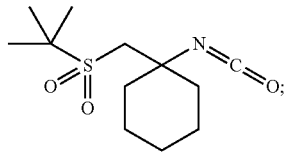

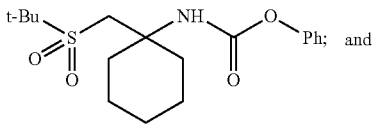

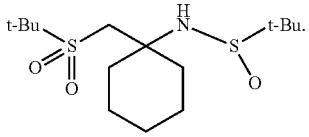

DETAILED DESCRIPTION

In one embodiment, the present invention relates to a process for preparing a compound of Formula I as described in Process 1.

In one embodiment, the present invention relates to a process for preparing a compound of Formula V as described in Process 2. A preferred compound of Formula V is one wherein R¹ is methyl or benzyl, more preferably methyl (i.e., compound Va)

In one embodiment, the present invention relates to a process for preparing a compound of Formula III as described in Process 3.

In one embodiment, the present invention relates to a process for preparing a compound of Formula VI as described in Process 14.

In one embodiment, the present invention relates to a process for preparing a compound of Formula VID as described in Process 16.

In one embodiment, the present invention relates to a process for preparing a compound of Formula VI as described in Process 19.

In one embodiment, the present invention relates to a process for preparing a compound of Formula VIBb as described in Process 20.

In one embodiment, the present invention relates to a process for preparing a compound of Formula VIN as described in Process 21.

In one embodiment, the present invention relates to preparing a compound of Formula IIIF using Process 4, Process 5, Process 6, Process 7, Process 8, Process 9, Process 10 or Process 11.

In one embodiment, the present invention relates to a process for preparing a compound of Formula VI using Process 12 or Process 13.

In one embodiment, the present invention relates to a process for preparing a compound of Formula VIB as described in Process 15.

In one embodiment, the present invention relates to a process for preparing a compound of Formula VID as described in Process 17.

In one embodiment, the present invention relates to a process for preparing a compound of Formula VIBa as described in Process 18.

In another embodiment, the present invention relates Process 1 wherein the compound of Formula II is prepared by the conversion of compound of Formula Va (i.e., the methyl ester of compound V) to the corresponding acid; the compound of Formula Va is prepared by Process 2 from the compound of Formula VI and the compound of Formula VII-1 (i.e., the compound of VII wherein $R^1$ is methyl), the compound of Formula VI is prepared by Process 14 from the compound of Formula VID; the compound of Formula VID is prepared by Process 16; and the compound of Formula III is prepared by Process 3, that is, a process for preparing a compound of Formula I comprising:

1) preparing the compound of Formula VID by Process 16;
2) treating VID according to Process 14 to obtain the compound of the Formula VI;
3) coupling the compound of Formula VI with the amine of Formula VII-1 as described in Process 2 to obtain the compound of Formula Va;
4) preparing the amine of Formula III according to Process 3;
5) converting the methyl ester of Formula Va to the free acid of Formula II;
6) coupling the acid of Formula II with the amine of Formula III to obtain the alcohol of Formula IV and oxidizing the alcohol according to Process 1.

In another embodiment, the present invention relates to a process for preparing a compound of Formula I comprising:

1) preparing the compound of Formula III by Process 3;
2) reacting the compound of Formula III with the protected amine of Formula VIIA to obtain the compound of Formula VIII;
3) preparing methyl ester Va by Process 2 and converting it to the free acid II;
4) removing the protecting group of VIII to obtain VIIIA and coupling VIIIA with acid II to obtain alcohol IV;
5) oxidizing the alcohol.

In another embodiment, the invention relates to the preparation of the compound of Formula VI comprising:

1) preparing sulfone VIN according to Process 21;
2) preparing imine VIP and reacting it with sulfone VIN to obtain the sulfone-sulfinamide of Formula VIQ, then converting VIQ to the free amine VIBb according to Process 20;
3) reacting VIBb with phenylchloroformate in the presence of a base to obtain the carbamate of Formula VIO, and reacting VIO with tent-leucine according to Process 19.

In Process 1 for the preparation of the compound of Formula I, the coupling of the intermediate acid of Formula II and the amine of Formula III is accomplished using standard peptide coupling methods known in the art, for example the use of 1-ethyl-3-(3-dimethylaminopropyl)-carbodiimide (EDCi) and 1-hydroxybenzotriazole (HOBt) in the presence of a base such as N,N-diisopropylethylamine (DIPEA). The use of the single diastereomer of the amine III results in the single diastereomer of the compound of Formula IV, which is crystallized from ethyl acetate/water in high purity. The process disclosed in the '968 publication formed a mixture of diastereomers in step 7; the mixture could not be crystallized and required a volumetrically inefficient precipitative isolation that did not remove any impurities. The presently claimed process allows for more volumetrically efficient isolation, a reduction in solvent use, an increase in reactor capacity, and the capability of removing impurities efficiently at this step.

The single diastereomer of the amine III can be replaced in the process by the diastereomer III-1. Furthermore, while the HCl salt is preferred for compound III or III-1, any suitable acid addition salt can be used.

The free acid of Formula II is prepared from the ester of Formula V by methods well known in the art, for example by treatment with NaOH. Preferred esters of Formula V are esters wherein $R^1$ is alkyl or benzyl; more preferably, $R^1$ is methyl.

In step 2 of Process 1, the alcohol of Formula IV is oxidized to the ketone of Formula I by one of a number of possible oxidation methods, including:

i) TEMPO (2,2,6,6-tetramethyl-1-piperidinyloxy, free radical) based oxidations, where TEMPO is:
A stoichiometric reagent, where TEMPO is disproportionated to its fully oxidized form;
A stoichiometric or catalytic reagent where TEMPO is used with an additional oxidant. Additional oxidants include bleach (sodium hypochlorite); permanganate (any salt); manganese dioxide; oxone, a peracid, such as meta-perchlorobenzoic acid; a peroxide, such as hydrogen peroxide or an alkyl-hydrogen peroxide, such as tert-butyl hydrogen peroxide; oxygen, either neat or as a component of a mixture of gas (e.g. air); rare-earth metals in the +4 oxidation state, such as ceric salts; iron salts in the +3 oxidation state; palladium salts in the +2 oxidation state, either alone or as a cooxidant with an additional stoichiometric oxidant; halogens in the oxidation state of 0 to +7; N-iodo, N-bromo or N-chloro succinimide type compounds; a quinone, such as benzoquinone; electrochemically
ii) An electrochemical oxidation;
iii) A sulfoxide or selenoxide based oxidation, such as a Swern or Moffatt type oxidation;
iv) A hypervalent halide oxidation, such as Dess-Martin periodinate or IBX (iodoxybenzoic acid), either stoichiometrically or catalytically with an stoichiometric co-oxidant;
v) A transition metal based oxidation, such as Ag, Ru, V, Mo, Cu, Co, Cr, Pb, Fe, Pd, or Mn, either stoichiometrically or catalytically with a stoichiometric co-oxidant;
vi) An Oppenauer type oxidation, where the stoichiometric oxidant is a ketone and a catalyst, such as $Al(OR)_3$;
vii) An enzyme based oxidation, such as alcohol dehydrogenase;
viii) Dioxirane based oxidations (e.g. DMDO)

A preferred oxidation method employs bleach as the oxidant and TEMPO as the catalyst. The compound of Formula IV has low solubility in many solvents: water wet methyl acetate was found to be one example of a suitable solvent for the oxidation.

In Process 2 for the preparation of the compound of Formula V, the free acid VI is coupled to the amine VII, wherein $R^1$ is as defined above, preferably alkyl, more preferably methyl, using standard peptide coupling methods known in the art, for example the use of EDCi and HOBt and a base such as N-methylmorpholine (NMM) in a water soluble solvent such as acetonitrile; other coupling reagents such as o-benzotriazol-1-yl-N,N,N',N',-tetramethyluronium hexaflourophosphate (HATU), bis(2-oxo-3-oxazolidinyl)phosphinic chloride (BOP—Cl) and carbonyl diimidazole (CDI) can also be used. In place of the usual aqueous workup upon completion of the coupling reaction, the present process comprises adding water directly to the resultant reaction solution, resulting in crystallization of compound V as the hydrate. Filtration of the crystallized solids leads to recovery of the hydrated V while the side products largely stay in the filtrate. The wet cake of the hydrate is then charged to a solvent such as ethyl acetate or toluene, and the solution is distilled to azeotropically remove most of the water. Once the water is reduced to a low level, a non-aqueous antisolvent such as heptanes is added to crystallize the anhydrous form of compound V.

Process 2 is advantageous because preferred compound Va ($R^1$ is methyl) exists as two polymorphs, a hydrated form and an anhydrous form. Because the hydrated form does not have a definite amount of water, it is difficult to obtain an accurate measure of purity through a wt/wt assay, however the process that forms the hydrated polymorph (step 2 of Process 2) provides improved control of impurities. Conversely, the anhydrous form can be accurately weighed, but the process for making it does not remove impurities as efficiently. Process 2 takes advantage of the desired properties of both methods while improving the overall efficiency of the reaction an a large scale; it eliminates the need for multiple aqueous washes typically associated with EDCi/HOBt amide bond coupling reactions.

Process 3 describes the preparation of the single diastereomer of the amine salt III required for the preparation of the compound of Formula I. Step 1 of Process 3 comprises condensing valeraldehyde and malonic acid in a solvent such as pyridine to obtain the α,β-unsaturated acid IIIB, followed in step 2 by reaction of IIIB under pressure with 2-methylpropene and an acid catalyst such as $H_2SO_4$ to obtain the ester IIIC. The ester IIIC is reacted with (S)—N-(-)-benzyl-α-methylbenzylamine, preferably at temperature range of −65 to −55° C. and in a solvent such as THF, to obtain the intermediate enolate. (S)—N-(-)-benzyl-α-methylbenzylamine is formed in situ by reacting (S)-benzyl-1-phenyl ethylamine and n-hexyl lithium before the addition of IIIC to the reaction mixture. (1S)-(+)-(10-camphorsulfonyl)-oxaziridine is then added to the enolate solution (no isolation is necessary) to obtain the β-amino-α-hydroxy ester IIID. A similar procedure is described in Beevers et al, *Bioorg. Med. Chem. Lett.*, 2002, 12, 641-643, however Beevers et al use a temperature of −78° C., compared to the more manageable −65 to −55° C. temperature used in the present process. In step 4, the ester IIID is treated with an acid such as trifluoroacetic acid to obtain the free acid, which is coupled (without isolation) with cyclopropylamine in the presence of a dehydrating agent such as EDCi/HOBt to obtain the amide IIIE. In step 5, the benzyl protecting groups on IIIE are removed, for example by a hydrogen source in the presence of a metal catalyst, such as hydrogen gas and palladium on carbon, to obtain the free amine IIIF. Treatment of IIIF with HCl provides the salt III.

Alternatively, in step 3, the reaction of IIIC with the lithium amide can be quenched with water or another proton source, the enolate can be re-formed to obtain IIID-1, which can then be treated with the oxaziridine to obtain IIID.

Other N-protected lithium amides can be used in step 3 provided that the chiral center at the N is set.

A procedure analogous to Process 3, using the appropriate reagent in step 3, can be used to prepare the compound of Formula IIIF-1 and its HCl salt, III-1.

Using methods known in the art, another acid addition salt can be substituted for HCl in step 5 of Process 3 to prepare other salts of IIIF and IIIF-1.

Process 4 for the preparation of compound IIIF comprises opening the ring of lactam IIIG to obtain the amino acid IIIH, for example by treatment with an acid, preferably HCl. Coupling of IIIH with cyclopropylamine is accomplished in a manner similar to that described in Process 3, step 4, and subsequent deprotection of the amino and hydroxyl groups (when $R^2$ and $R^3$ are not H) is carried out by procedures known in the art. Preferred $R^2$ groups are alkyl and benzyl; preferred $R^3$ groups are alkyl and benzyl.

Process 5 for the preparation of compound IIIF comprises reducing the enamine III-1 by asymmetric hydrogenation to obtain IIIJ and converting IIIJ to the carboxylic acid IIIH-1. Coupling of IIIH-1 with cyclopropylamine is accomplished in a manner similar to that described in Process 3, step 4, and subsequent deprotection of the amino and hydroxyl groups (when $R^2$, $R^6$ and $R^7$ are not H) is carried out by procedures known in the art. Preferred $R^2$ groups are alkyl and benzyl; preferred $R^6$ and $R^7$ groups are alkyl and benzyl.

Process 6 for the preparation of compound IIIF comprises hydroxylation of IIIK to obtain IIIL, for example by treatment with LiHMDS and oxaziridine, and conversion of IIIL to the carboxylic acid IIIH-2. Coupling of IIIH-2 with cyclopropylamine is accomplished in a manner similar to that described in Process 3, step 4, and subsequent deprotection of the amino group (when $R^6$ and $R^7$ are not H) is carried out by procedures known in the art. Preferred $R^6$ and $R^7$ groups are alkyl and benzyl.

Process 7 for the preparation of compound IIIF comprises reducing the nitro group of IIIM to obtain amino acid IIIN, resolving IIIN by procedures known in the art to obtain IIIO, and converting IIIO to the carboxylic acid IIIH-3. Coupling of IIIH-3 with cyclopropylamine is accomplished in a manner similar to that described in Process 3, step 4, and subsequent deprotection of the hydroxyl group (when $R^2$ is not H) is carried out by procedures known in the art. Preferred $R^2$ groups are alkyl and benzyl.

Process 8 for the preparation of compound IIIF comprises reducing the α-keto compound IIIP to obtain IIIL, which is then treated in a manner similar to that described in Process 6 to obtain IIIF. Preferred $R^6$ and $R^7$ groups are alkyl and benzyl.

Process 9 for the preparation of compound IIIF comprises converting compound IIIQ to obtain amine IIIJ, for example by a Mitsunobu type reaction. IIU, is then treated in a manner similar to that described in Process 5 to obtain IIIF.

Process 10 for the preparation of compound IIIF comprises opening the ring of epoxide IIIR with a nitrogen source such as ammonia or an azide to obtain IIIS, and conversion of IIS to the carboxylic acid IIIH-4. Coupling of IIIH-4 with cyclopropylamine is accomplished in a manner similar to that described in Process 3, step 4. $R^8$ is preferably H, alkyl or benzyl.

Process 11 for the preparation of compound IIIF comprises treating an aziridine IIIT with an oxygen source such as an alkoxide to obtain IIIU, and conversion of IIIU to the carboxylic acid IIIH-5. Coupling of IIIH-5 with cyclopropylamine is accomplished in a manner similar to that described in Process 3, step 4, and subsequent deprotection of the amino and hydroxyl groups (when $R^2$ and $R^6$ are not H) is carried out by procedures known in the art. $R^2$ is preferably alkyl or benzyl, and $R^6$ is preferably alkyl or benzyl.

Processes 12 and 13 prepare the urea VI by either the displacement of a leaving group (e.g., compounds VIA wherein P is, for example, Ms or Ts) (Process 12) or the opening of an aziridine ring (Process 13) with a sulfur nucleophile of the formula $(CH_3)_3C-S^-M^+$, wherein M is H or a metal such as Na, Li or K, followed by oxidation to obtain VIB. The compound of Formula VIB is then converted to the primary amine VIBb (i.e., $R^6$ and $R^7$ are both H) by methods known in the art. The amine intermediate VIBb is then coupled with tert-leucine in the presence of a reagent such as phosgene or a phosgene equivalent to obtain VI. $R^6$ and $R^7$ are preferably independently H, alkyl or benzyl.

In Process 14, the urea VI is prepared by subjecting compound VID to a Curtius-type rearrangement, for example by treating with a reagent such as diphenylphosphoryl azide (DPPA) to obtain the isocyanate VIE. The isocyanate does not need to be isolated before reacting with S-tent-leucine to obtain the compound VI.

Process 15 provides an alternative route to compound VIB comprising condensing cyclohexanone with a sulfonyl compound of the formula $(CH_3)_3C-SO_2-CH_2-R^{10}$ (or $(CH_3)_3C-SO-CH_2-R^{10}$ or $(CH_3)_3C-S-CH_2-R^{10}$ to obtain the corresponding sulfinyl or thio analogs), wherein $R^{10-}$ is as defined above. The resulting unsaturated compound VIF is then reduced to the compound VIB; for example, when $R^{10}$ is —C(O)OH, VIF can be treated with a nitrogen nucleophile such as $HN(R^5)(R^6)$, followed by decarboxylation.

In Process 16 for the preparation of the intermediate acid/sulfone compound VID, step 1 comprises treating commercially available cyclohexane carboxylic acid, methyl ester (VIG), with a strong base such as lithium diisopropyl amide, then with chlorotrimethylsilane to obtain the trimethylsilyl enolate VIH. Alternatively, other esters of cyclohexane carboxylic acid, cyclohexane carbonitrile and other carbonyl derivatives of cyclohexane can be used in step 1 in place of VIG. The reaction solution containing VIH can undergo solvent exchange and concentration, but VIH does not need to be isolated before continuing with the procedure. The enolate is alkylated with tert-butyl chloromethyl sulfide using procedures known in the art (see Beight et al, *Bioorg. Med. Chem. Lett.*, 1996, 6, 2053-2058) to obtain the ester/sulfone VIJ.

In step 2 of Process 16, the ester is hydrolyzed to the free acid, VIK, for example by treatment with a base such as LiOH, NaOH, KOH, or CsOH, by hydrolysis under Bronsted or Lewis acidic conditions, or by enzyme-mediated hydrolysis. A preferred method is by treatment with NaOH. In step 3, the thioether portion of VIK is oxidized to the acid/sulfone VID, for example by treatment with potassium peroxymonosulfate (Oxone®), m-chloroperoxybenzoic acid, or dimethyl dioxirane (DMDO).

Process 17 is similar to Process 16, except that steps 2 and 3 are reversed, that is, the thioether portion is oxidized to the sulfone, then the ester is hydrolyzed to the acid.

Process 18 for the preparation of isocycante VIE comprises reacting commercially available cyclohexanone with an amine $R^6NH_2$ (wherein $R^6$ is as define dabove) to obtain the imine VIM, then alkylating VIM with $(CH_3)_3C-SO_2-CH_2-Li$ (VIN) to obtain VIBa. The amine is deprotected to the primary amine and converted to the desired isocyanate.

Process 19 for the preparation of the urea of formula VI comprises treating an amine of formula VIBb with phenylchloroformate in the presence of a base such as DIPEA to obtain the carbamate VIO, which is preferably purified by crystallization. VIO is then reacted with tert-leucine in the presence of a base such as 1,1,3,3-tetramethylguanidine. The resultant compound VI is preferably purified by crystallization.

Process 20 for the preparation of the amine VIBb comprises condensing cyclohexanone with tert-butyl sulfonamide in the presence of a dehydrating agent such as $Ti(OEt)_4$ to obtain imine VIP. The imine is then treated with $(CH_3)_3C-SO_2-CH_2-Li$ in a Mannich type reaction to obtain the sulfone-sulfinamide compound VIQ; VIQ is hydrolyzed with HCl to obtain the HCl salt, then treated with a base such as NaOH to obtain VIBb.

Process 21 for the preparation of VIN comprises oxidizing tert-butylthiomethyl ether with hydrogen peroxide and sodium tungstate at a temperature below about 30° C. to obtain VIR; keeping the temperature below about 30° C. avoids volatization and loss of tert-butylthiomethyl ether. VIR is then reacted with n-butyl lithium at a temperature of about 0° C.

Compared to steps S1-S5 of the process disclosed in the '968 publication and summarized in the background portion of this specification, Processes 19, 20 and 21 have several advantages. The product of S1, an unstable compound, is isolated in the '968 process, but is directly reacted to form a more stable intermediate in the present Process 20. The formation of the lithiated sulfone and the subsequent imine addition in Process 21 are carried out at about 0° C., while in the process in the '968 publication, the similar reaction (S2) is carried out at −78° C. In Process 19, the reagent used for the urea formation is phenylchloroformate, rather than phosgene as used in S4 in the process of the '968 publication. In the process disclosed in the '968 publication, the isolated intermediates are purified by column chromatography, while purification in Processes 19-21 is accomplished by crystallization.

Process 22 for the preparation of the compound of Formula I preferably comprises preparing intermediate V by the process described in Process 2, followed by converting the methyl ester V to the free acid II by methods known in the art, for example by treatment with a base such as NaOH, then coupling the acid II with an amine III and oxidizing the resulting alcohol as described in Process 1.

Process 23 for the preparation of the compound of Formula I uses intermediates similar to those described in Process 22, but combines them in a different order. A nitrogen-protected amine of Formula VIIA, wherein PG is a group such as t-butylcarbonyl (BOC) or carbobenzyloxy (CBZ), is reacted with an amino alcohol of Formula III to obtain a compound of Formula VIII, which is then deprotected and reacted with an acid of Formula VI to obtain the alcohol of Formula IV. The alcohol of Formula IV is then oxidized to obtain the compound of Formula I as described for Process 1.

Process 24 for the preparation of the compound of Formula VI comprises the reaction of the imine of Formula VIP with the sulfone of Formula VIN according to Process 20 to obtain the amine VIBb, followed by reaction of VIBb with phenylchloroformate, then tert-leucine as described in Process 19. Preferably, VIP is prepared as described in Process 20, and the sulfone VIN is prepared as described in Process 21.

Process 25 for the preparation of the compound of Formula IV comprises coupling the acid of Formula IX (known in the art) with the amine of Formula III, using standard peptide coupling methods, and deprotecting the resultant amine X using known methods to obtain the amine compound of Formula XI. The amine of Formula XI is reacted with the isocyanate VIE to obtain the compound of Formula IV.

In the specification, the following abbreviations are used in addition to those identified above: Me=methyl, Et=ethyl, Bu=butyl, Ms=mesyl=methanesulfonyl, Ts=tosyl=toluenesulfonyl, Ph=phenyl; THF=tetrahydrofuran; LDA=lithium diisopropyl amide; TMSCl=chlorotrimethyl silane; MTBE=methyl tert-butyl ether; RT=room temperature; TFA=trifluoroacetic acid; 2-MeTHF=2-methyl tetrahydrofuran.

As used herein, the following terms are as defined below unless otherwise indicated:

Alkyl means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain.

"Alkenyl" means means a straight or branched aliphatic hydrocarbon group containing at least one carbon-carbon double bond and comprising about 2 to about 15 carbon atoms in the chain. Preferred alkenyl groups have about 2 to about 12 carbon atoms in the chain; and more preferably about 2 to about 6 carbon atoms in the chain. "Lower alkenyl" means about 2 to about 6 carbon atoms in the chain which may be straight or branched. Non-limiting examples of suitable alkenyl groups include ethenyl, propenyl, n-butenyl, 3-methylbut-2-enyl, n-pentenyl, octenyl and decenyl. A preferred alkenyl group is allyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

The compounds of Formula IIIF and IIIF-1 can form salts which are also within the scope of this invention. The term "salt(s)", as employed herein, denotes acidic salts formed with inorganic and/or organic acids. Pharmaceutically acceptable (i.e., non-toxic, physiologically acceptable) salts are preferred, although other salts are also useful. Salts of the compounds of the Formula IIIF and IIIF-1 may be formed by known reactions, for example by reacting a compound of Formula IIIF or IIIF-1 with an amount of acid, such as an equivalent amount, in a medium such as one in which the salt precipitates or in an aqueous medium.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Preparation of Compound VIJ

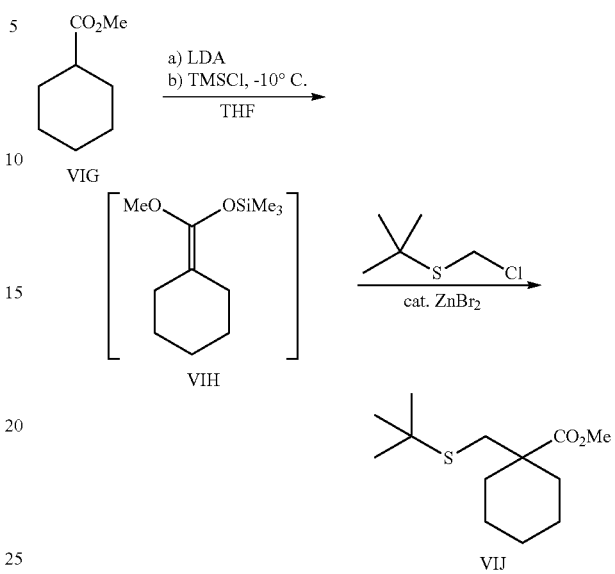

LDA was made by slowly charging n-butyl lithium (2.5 M, 159 kg) to diisopropyl amine (60 kg) dissolved in THF (252 kg), keeping the temperature at about −20° C., followed by agitation at this temperature for about 30 min. To this solution was charged cyclohexane carboxylic acid, methyl ester (70 kg), keeping the temperature below −10° C. The mixture was agitated at this temperature for about 2 h. To the resulting enolate was charged TMSCl (64.4 kg). The mixture was agitated at −10 to −20° C. for about 30 min, and then heated to about 25° C. and held at this temperature to allow for conversion to the silylenol ether Compound VIH. The reaction mixture was solvent exchanged to n-heptane under vacuum, keeping the temperature below 50° C., resulting in the precipitation of solids. The solids were filtered and washed with n-heptane, and the wash was combined with the n-heptane reaction mixture. The n-heptane mixture of Compound VIH was concentrated under vacuum and diluted with $CH_2Cl_2$.

In a separate reactor was charged $CH_2Cl_2$ (461 kg) and anhydrous $ZnBr_2$ (14.5 kg). The temperature of the zinc slurry was adjusted to about 20° C. To the zinc slurry was simultaneously charged the solution of Compound VIH and 2-chloromethylsulfanyl-2-methyl-propane (63.1 kg, ref: *Bioorg. Med. Chem. Lett,* 1996, 6, 2053-2058), keeping the temperature below 45° C. After complete addition, the mixture was agitated for about 1.5 h at 35 to 45° C., after which the reaction mixture was cooled to 10 to 15° C. A solution of dilute aqueous HCl was then charged, keeping the temperature between 0 and 15° C., followed by a separation of the aqueous and organic layers (desired compound in organic layer). The organic layer was washed with aqueous $NaHCO_3$ and water. The organic layer was solvent exchanged to methanol by vacuum distillation, keeping the temperature below 35° C., and kept as a solution in methanol for further processing to Compound VIK. Active Yield of Compound VIJ=69.7 kg (molar yield=57.9%).

Preparation of Compound VIK

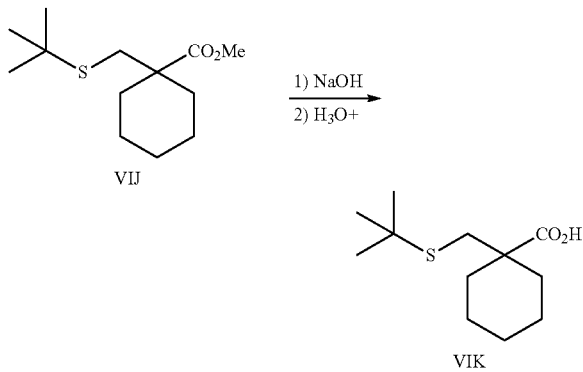

To a fresh reactor was charged Compound VIJ (99.8 kg active in a methanol solution), water (270 kg), NaOH (70 kg), and methanol (603 kg). The mixture was heated to ~70° C. and agitated at this temperature for about 16 h. Upon conversion to the sodium salt of Compound VIK, the reaction mixture was concentrated under vacuum, keeping the temperature below 55° C., and then cooled to about 25° C. Water and MTBE were then charged, agitiated, and the layers were separated (product in the aqueous layer). The product-containing aqueous layer was further washed with MTBE.

$CH_2Cl_2$ was charged to the aqueous layer and the temperature was adjusted to ~10° C. The resultant mixture was acidified to a pH of about 1.5 with HCl, agitated, settled, and separated (the compound was in the organic layer). The aqueous layer was extracted with $CH_2Cl_2$, and the combined organic layers were stored as a $CH_2Cl_2$ solution for further processing to Compound VID. Active yield of Compound VIK=92.7 kg (molar yield=98.5 kg). MS Calculated: 230.13. MS Found (ES-, M-H): 229.11.

Preparation of Compound VID

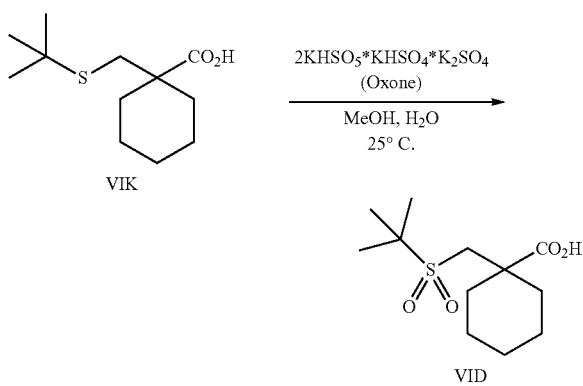

To a reactor was charged water (952 kg), Oxone® (92.7 kg), and Compound VIK (92.7 kg active as a solution in $CH_2Cl_2$). The reaction mixture was agitated for about 24 h at a temperature of about 15° C., during which time Compound VIK oxidized to sulfone Compound VID. The excess Oxone® was quenched with aqueous $Na_2S_2O_5$, the reaction mixture was settled and the layers separated; the aqueous layer was back-extracted with $CH_2Cl_2$, and the combined product-containing organic layers were washed with water.

The resultant solution was then concentrated under vacuum. To precipitate Compound VID, n-heptane was charged, and the resulting slurry was agitated for about 60 min at a temperature of about 30° C. The reaction mixture was filtered, and the wet cake was washed with n-heptane. The wet cake was redissolved in $CH_2Cl_2$, followed by the addition of n-heptane. The resultant solution was then concentrated under vacuum, keeping the temperature below 35° C., to allow for product precipitation. The resultant solution was cooled to about 0° C. and agitated at this temperature for about 1 h. The solution was filtered, the wet cake was washed with n-heptane, and dried under vacuum at about 45° C. to yield 68.7 kg Compound VID (molar yield=65.7%). MS Calculated: 262.37. MS Found (ES-, M-H): 261.09

Preparation of Compound VI

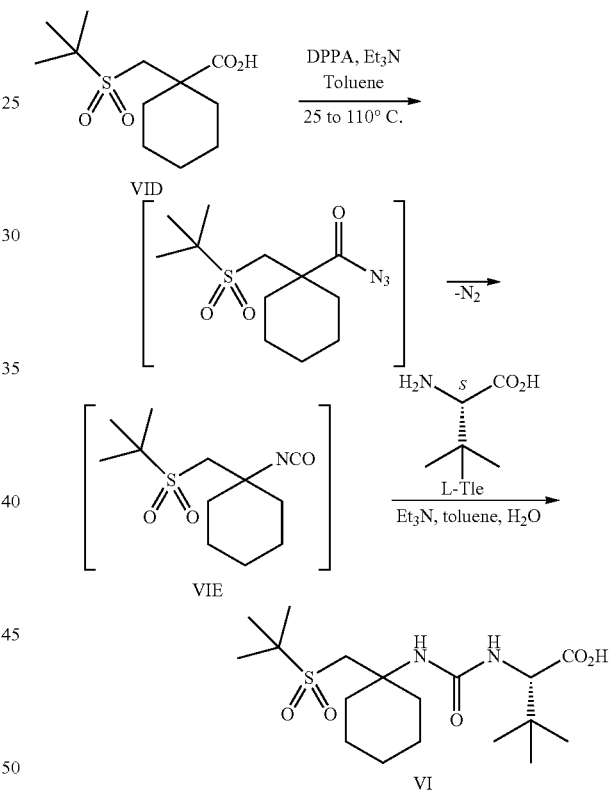

To a reactor was charged Compound VID (68.4 kg), toluene (531 kg), and $Et_3N$ (31 kg). The reaction mixture was atmospherically refluxed under Dean-Stark conditions to remove water (target KF<0.05%). The reaction temperature was adjusted to 80° C., DPPA (73.4 kg) was charged over 7 h, and the mixture was agitated for an additional 2 h. After conversion to isocyanate Compound VIE via the azide, the reaction mixture was cooled to about 0 to 5° C. and quenched with aqueous $NaHCO_3$. The resultant mixture was agitated, settled and the layers were separated. The aqueous layer was extracted with toluene, and the combined isocyante Compound VIE organic layers were washed with water.

In a separate vessel was charged L-tert-Leucine (L-Tle, 30.8 kg), water (270 kg), and $Et_3N$ (60 kg). While keeping the temperature at about 5° C., the toluene solution of Compound VIE was transferred to the solution of L-Tle. The reaction mixture was stirred at 0 to 5° C. for about 5 h, at which time the mixture was heated to 15 to 20° C. and agitated at this temperature for 2 h to allow for conversion to urea Compound VI.

The reaction was quenched by the addition of aqueous NaOH, keeping the temperature between 0 and 25° C. The reaction mixture was separated, and the organic layer was extracted with water. The combined Compound VI-containing aqueous layers were washed with toluene, and acidified to pH 2 by the addition of HCl, at which time the product precipitated from solution. The reaction mixture was filtered, washed with water and dried under vacuum at 65 to 70° C. to yield 79.7 kg crude Compound VI (molar yield 52.7%). MS Calculated: 390.54. MS Found (ES−, M−H): 389.20.

Compound VI is further purified by slurrying in $CH_3CN$ at reflux (about 80° C.), followed by cooling to RT. Typical recovery is 94%, with an increase in purity from about 80% to 99%.

Preparation of Compound Va

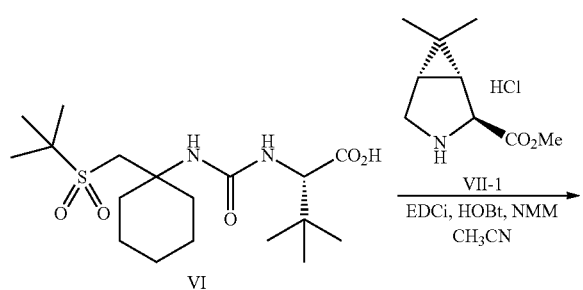

To a reactor was charged Compound VI (87.6 kg), Compound VII-1 (48.2 kg), HOBt (6 kg) and $CH_3CN$ (615 kg). The reaction mixture was cooled to about 5° C., and NMM (35 kg) and EDCi (53.4 kg) were charged. The reaction was heated to 20 to 25° C. for about 1 h, and then to 35 to 40° C., at which time water was charged to crystallize Compound Va. The reaction mixture was cooled to 5° C. and held at this temperature for about 4 h. Compound Va was filtered and washed with water. XRD data for the hydrated polymorph of Va is as follows:

| Diffraction Angle (Degrees 2 Theta, ±0.2) | d spacing (Angstroms) | Relative Intensity Strong, Medium, Weak |
|---|---|---|
| Four most distinctive peaks | | |
| 7.3 | 12.1 | W |
| 8.6 | 10.3 | S |
| 12.9 | 6.9 | W |
| 22.3 | 4.0 | W |
| Second four most distinctive peaks | | |
| 18.6 | 4.8 | W |
| 27.4 | 3.3 | W |
| 28.5 | 3.1 | W |
| 29.3 | 3.0 | W |
| Third four most distinctive peaks | | |
| 11.6 | 7.6 | M |
| 14.6 | 6.1 | W |
| 15.3 | 5.8 | W |
| 17.1 | 5.2 | W |

The Compound Va wet cake was charged to a fresh vessel and was dissolved in ethyl acetate at 25 to 30° C. The solution was washed with an aqueous HCl solution, aqueous $K_2CO_3$ solution, and brine. The solution was then concentrated under vacuum, keeping the temperature between 35 to 50° C. Additional ethyl acetate was charged, and the solution was heated to 65 to 70° C. While keeping the temperature at 65 to 70° C., n-heptane was charged, followed by cooling the resultant solution to 0 to 5° C. Compound Va was filtered and washed with an ethyl acetate/n-heptane mix.

The wet cake was dried under vacuum between 55 to 60° C. to yield 96.6 kg crystalline Compound Va (molar yield 79.2%). MS Calculated: 541.32. MS Found (ES+, M+H): 542.35.

XRD data for the anhydrous polymorph of Va is as follows:

| Diffraction Angle (Degrees 2 Theta, ±0.2) | d spacing (Angstroms) | Relative Intensity Strong, Medium, Weak |
|---|---|---|
| Four most distinctive peaks | | |
| 6.0 | 14.7 | W |
| 10.0 | 8.8 | S |
| 10.5 | 8.5 | M |
| 17.8 | 5.0 | S |
| Second four most distinctive peaks | | |
| 13.3 | 6.6 | W |
| 16.2 | 5.5 | M |
| 21.7 | 4.1 | W |
| 22.8 | 3.9 | W |
| Third four most distinctive peaks | | |
| 9.4 | 9.4 | S |
| 12.5 | 7.1 | W |
| 17.0 | 5.2 | M |
| 19.7 | 4.5 | W |

Preparation of Compound IIIB

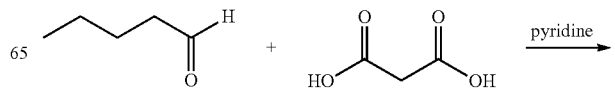

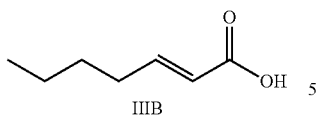

IIIB

Pyridine (92 L) was charged to the reactor and was cooled to 5° C. To the cooled pyridine was slowly charged malonic acid (48.5 kg) and valeraldehyde (59 L), keeping the temperature below 25° C. The reaction was stirred between 25 to 35° C. for at least 60 h. After this time, $H_2SO_4$ was charged to acidify, keeping the temperature below 30° C. The reaction mixture was then extracted into MTBE. The organic layer was washed with water. In a separate reactor was charged water and NaOH. The MTBE solution was charged to the NaOH solution, keeping the temperature below 25° C., and the desired material was extracted into the basic layer. The basic layer was separated and the organic layer was discarded. MTBE was charged, the mixture was agitated, settled, and separated, and the organic layer was discarded. To the resultant solution (aqueous layer) was charged water and $H_2SO_4$ to acidify, keeping the temperature between 10 to 15° C. To the acidified mixture was charged MTBE, keeping the temperature below 25° C. The resultant solution was agitated, settled, and separated, and the aqueous layer was discarded. The product-containing organic layer was washed with water and was concentrated under vacuum, keeping the temperature below 70° C., to yield 45.4 kg Compound IIIB (molar yield=76.2%) as an oil. Compound Reference: Concellon, J. M.; Concellon, C *J. Org. Chem.*, 2006, 71, 1728-1731

Preparation of Compound IIIC

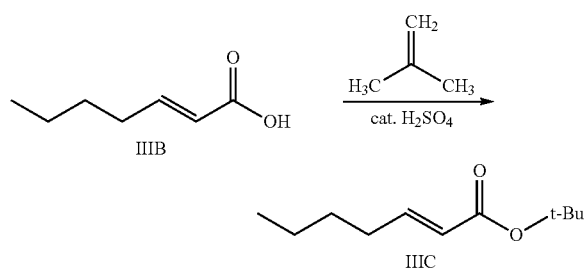

To a pressure vessel was charged Compound IIIB (9.1 kg), heptane (9 L), and $H_2SO_4$ (0.5 kg). The pressure vessel was sealed and isobutylene (13.7 kg) was charged, keeping the temperature between 19 to 25° C. The reaction mixture was agitated at this temperature for about 18 h. The pressure was released, and a solution of $K_2CO_3$ was charged to the reaction mixture, which was agitated and settled, and the bottom aqueous layer was then separated. The resultant organic solution was washed with water and distilled under vacuum (temp below 45° C.) to yield 13.5 kg Compound IIIC (molar yield=88.3%) as a yellow oil.

Preparation of Compound IIID

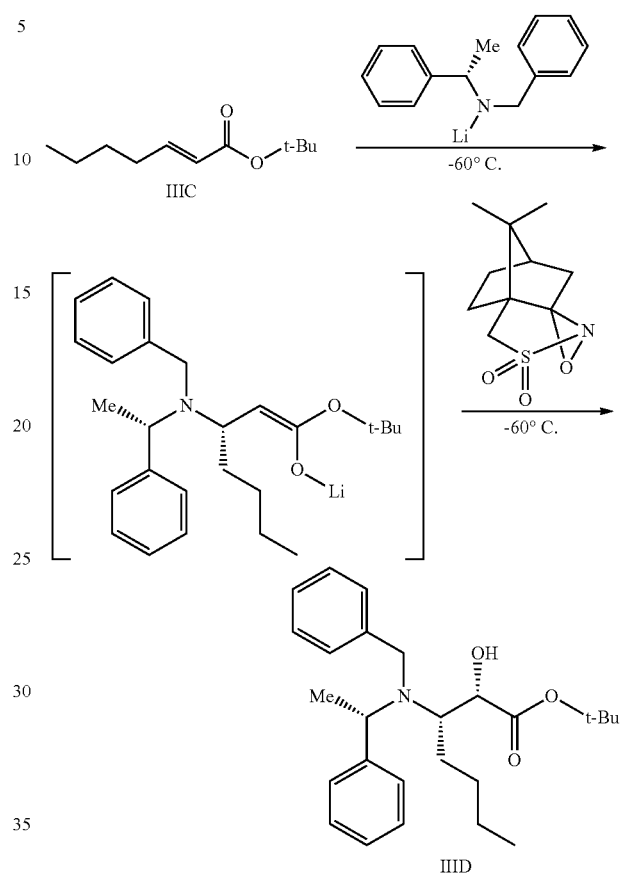

To a reactor capable of maintaining a temperature of −60° C. was charged (S)-benzyl-1-phenyl ethylamine (18 kg) and THF (75 L). The reaction mixture was cooled to −60° C. To the mixture was charged n-hexyl lithium (42 L of 2.3 M in heptane) while maintaining a temperature of −65 to −55° C., followed by a 30 min agitation within this temperature range. To the in situ-formed lithium amide was charged Compound IIIC over 1 h, keeping the temperature between −65 to −55° C. The reaction mixture was agitated at this temperature for 30 min to allow for conversion to the enolate intermediate. To the resultant reaction mixture was charged (+)-camphorsulfonyl oxaziridine (24 kg) as a solid, over a period of 2 h, keeping the temperature between −65 to −55° C. The mixture was agitated at this temperature for 4 h.

The resultant reaction mixture was quenched by the addition of acetic acid (8 kg), keeping the temperature between −60 to −40° C. The mixture was warmed to 20 to 25° C., then charged into a separate reactor containing heptane. The resultant mixture was concentrated under vacuum, keeping the temperature below 35° C. Heptane and water were charged to the reaction mixture, and the precipitated solids were removed by filtration (the desired compound is in the supernatant). The cake was washed with heptane and this wash was combined with the supernatant. The heptane/water solution was agitated, settled, and separated to remove the aqueous layer. An aqueous solution of $H_2SO_4$ was charged, and the mixture was agitated, settled, and separated. The heptane layer was washed with a solution of $K_2CO_3$.

The heptane layer was concentrated under reduced pressure, keeping the temperature below 45° C., and the resulting oil was diluted in toluene, yielding 27.1 kg (active) of Compound IIID (molar yield=81.0%). MS Calculated: 411.28. MS Found (ES+, M+H): 412.22.

A similar procedure for this step was reported in: Beevers, R, et al, *Bioorg. Med. Chem. Lett.* 2002, 12, 641-643.

Preparation of Compound IIIE

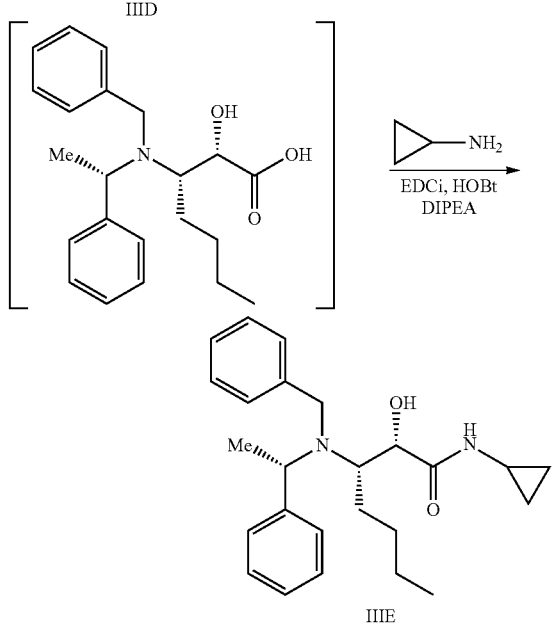

Toluene (324 L) and a toluene solution of Compound IIID (54.2 kg active) was charged to the reactor. TFA (86.8 kg) was charged over about 1.5 h, keeping the temperature below 50° C. The reaction mixture was agitated for 24 h at 50° C. The reaction mixture was cooled to 15° C. and water was charged. NaOH was slowly charged, keeping the temperature below 20° C., to adjust the batch to a pH between 5.0 and 6.0. The reaction mixture was agitated, settled, and separated; the aqueous layer was discarded. The organic layer was concentrated under vacuum, keeping the temperature below 40° C., and the resulting acid intermediate (an oil), was dissolved in 2-MeTHF.

In a separate reactor, 2-MeTHF (250 L), HOBt (35.2 kg), and EDCi-HCl (38.0 kg) were charged and the mixture was adjusted to a temperature between 0 to 10° C. DIPEA (27.2 kg) was charged, keeping the mixture within this temperature range. The mixture was agitated for 5 min, followed by the addition of cyclopropyl amine (11.4 kg), keeping the temperature between 0 to 10° C.

To this solution was charged the 2-MeTHF/acid intermediate solution, keeping the resultant solution between 0 to 10° C. The resultant mixture was heated to 25 to 35° C., and was agitated at this temperature for about 4 h. The reaction mixture was cooled to about 20° C., and was washed with aqueous citric acid, aqueous K$_2$CO$_3$, and water. The solvent was exchanged to n-heptane, and the desired compound was crystallized from a mix of n-heptane and toluene by cooling to 0° C. The crystalline product was filtered, washed with n-heptane, and dried to yield 37.1 kg Compound IIIE (molar yield=70.7%). MS Calculated: 394.26. MS Found (ES+, M+H): 395.22.

Preparation of Compound III

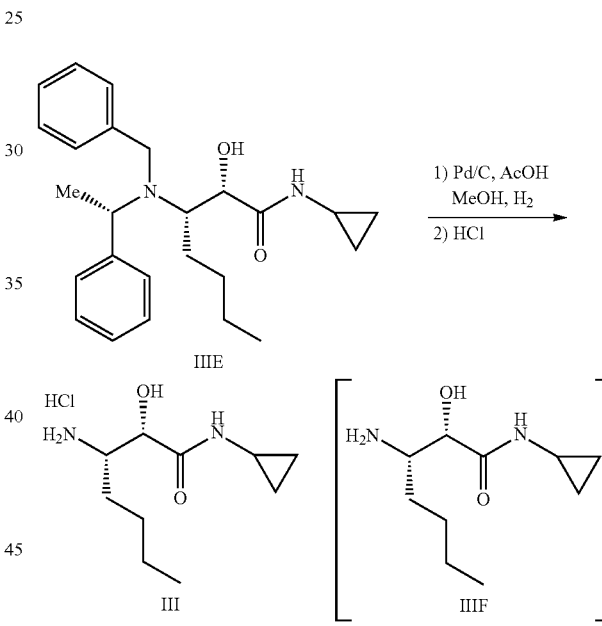

To a pressure reactor was charged acetic acid (1.1 kg), methanol (55 kg), and Compound IIIE (10.9 kg). In a separate vessel, Pd/C (50% water wet, 0.5 kg) was suspended in methanol (5 kg). The Pd/C suspension was transferred to the solution containing Compound IIIE. The resultant mixture was pressurized to 80 psi with hydrogen, and agitated at 60° C. for 7 h. The reaction mixture was then purged with nitrogen, and the Pd/C catalyst was filtered off. The resultant solution was concentrated under vacuum and adjusted to about 20° C. MTBE was charged, and the resultant solution was brought to reflux. Concentrated HCl (3 L) was charged and the product was crystallized by cooling the reaction mixture to about 3° C. The desired compound was filtered, washed with MTBE, and dried under vacuum, keeping the temperature below 40° C. to yield 5.5 kg Compound III (molar yield=83.0%). MS Calculated (free base): 200.15. MS Found (ES+, M+H): 201.12.

Preparation of Compound II

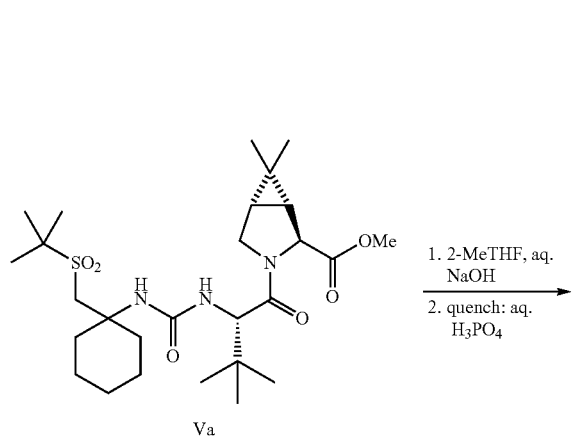

Preparation of Compound IV

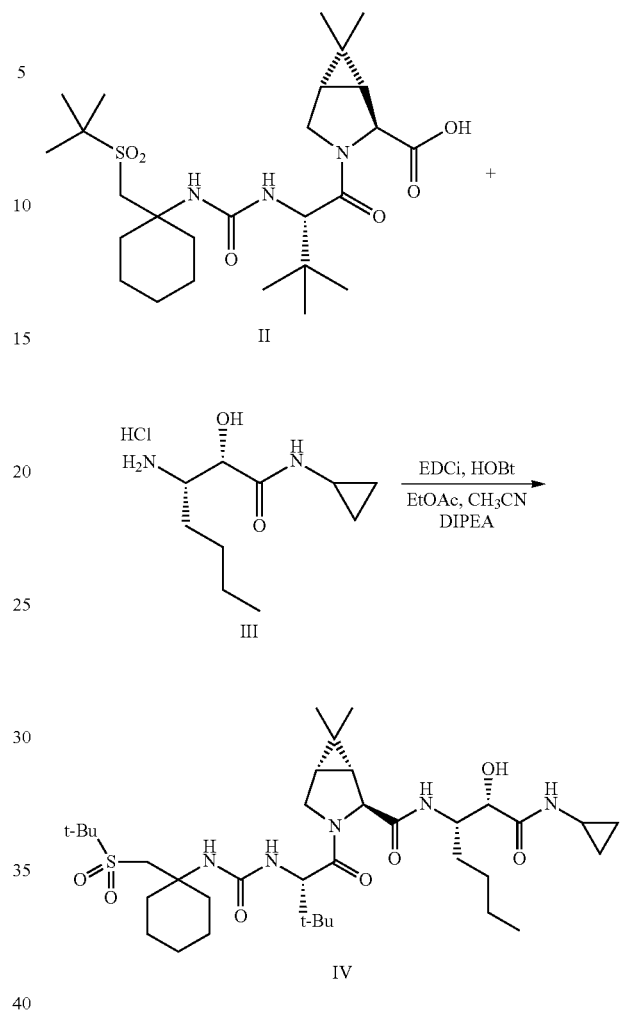

Compound Va (119.3 kg) was dissolved in 2-MeTHF (720 kg) and water (180 kg). To this solution was charged 50% NaOH (21.4 kg) while maintaining a temperature between 20 and 30° C. The reaction mixture was then agitated for about 7 h at a temperature between 50 and 60° C. The reaction mixture was cooled to a temperature between 20 and 30° C.

The pH of the reaction mixture was adjusted to 1.5-3.0 with dilute phosphoric acid, maintaining a temperature between 20 and 30° C. The resultant mixture was agitated for 10 min, settled for 30 min, and the bottom aqueous layer was separated and removed. The top organic layer was washed with water, followed by concentration by atmospheric distillation.

The concentrated solution was solvent exchanged to $CH_3CN$ by continuous atmospheric distillation, and crystallized by cooling to 0° C. The crystalline product was filtered, washed with $CH_3CN$, and dried under vacuum at a temperature between 45 and 55° C. to yield 97.9 kg Compound II (molar yield=83.7%). MS Calculated: 527.30. MS Found (ES+, M+H): 528.29.

Compound II (21.1 kg), Compound III (9.9 kg), HOBt (3.2 kg) and EDCi (11.2 kg) were charged to the vessel, followed by $CH_3CN$ (63 kg), ethyl acetate (20 kg) and water (1.5 kg). The reaction mixture was agitated and the heterogeneous mixture was cooled to −5 to +5° C. DIPEA (11.2 kg) was charged to the reaction mixture, maintaining a temperature between −5 to +5° C. and the mixture was agitated at a temperature of −5 to +5° C. for 1 h. The resultant reaction mixture was warmed to 20 to 30° C. and agitated for 2 to 3 h.

The resultant product was extracted with aqueous HCl, aqueous $K_2CO_3$, and water.

The desired product was crystallized from ethyl acetate by cooling from reflux (78° C.) to about 0° C. The crystalline product was filtered and dried at 30° C. under vacuum to yield 23.1 kg Compound IV (molar yield=81.3%). MS Calculated: 709.44. MS Found (ES+, M+H): 710.47.

Preparation of Compound I

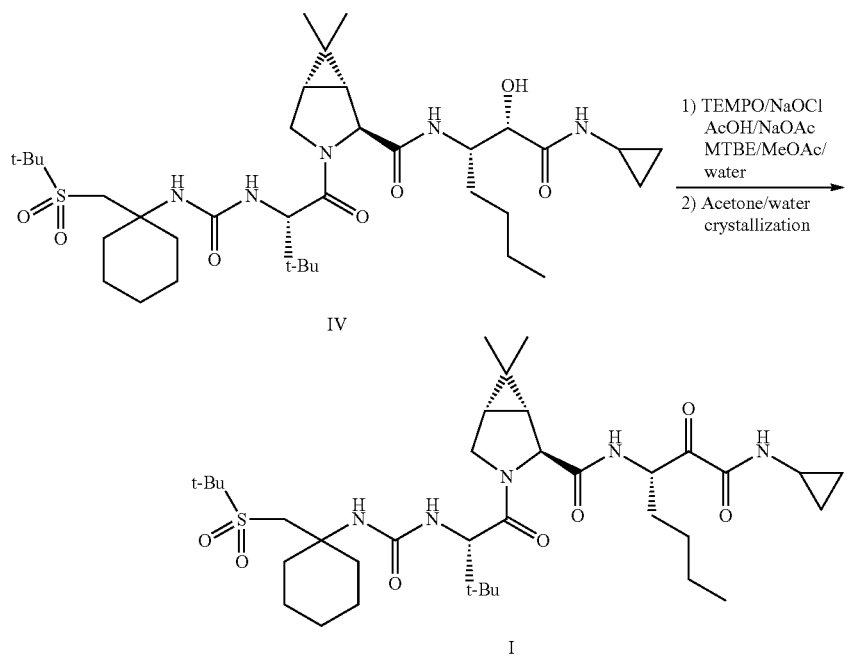

Compound IV (22.5 kg), TEMPO (5 kg), NaOAc (45 kg), methyl acetate (68 L), MTBE (158 L), water (23 L) and acetic acid (22.5 L) were charged to the reactor. The reaction mixture was stirred at 20-30° C. to allow for dissolution of the solids, and was then cooled to 5-15° C. NaOCl solution (1.4 molar equivalents) was charged to the reaction mixture, keeping the temperature at about 10° C. After complete addition of NaOCl, the reaction mixture was agitated at 10° C. for 2 h.

The reaction was quenched by washing with a buffered sodium ascorbate/HCl aqueous solution, followed by a water wash.

The reaction mixture was solvent exchanged to acetone under vacuum, keeping the temperature below 20° C.; the desired product was crystallized by the addition of water, and dried under vacuum, keeping the temperature below 40° C. to yield 18.6 kg Compound I (molar yield=82.7%). MS Calculated: 707.43. MS Found (ES+, M+H): 708.44.

Preparation of Compound VIR

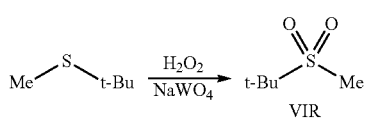

Na$_2$WO$_4$ (2.2 kg, 0.013 eq.) was added to water (45 L), followed by t-butyl methyl sulfide (54.8 kg, 1 eq.). H$_2$O$_2$ (115 kg, 2.2 eq.) was added with stirring, under N$_2$, with the reaction temperature being maintained below 30° C. After completion of the reaction (monitored by HPLC), NaCl (50 kg) was added, then MTBE (214 L) and the reaction was maintained at 22±3° C. for 15 min. The organic layer was separated and the aqueous layer was re-extracted with MTBE (110 L). The combined organic layers were distilled to reduce volume, and the distillate was cooled slowly to 10-15° C. to crystallize the desired product. The resultant mixture was cooled to 7±3° C. and heptane (110 L) was added; after 1 h, the mixture was cooled to 0±3° C. After 1 h, the solid was isolated by centrifugation, washed twice with heptane (2×33 L) and dried at 30° C. The product VIR was obtained in 85% yield. MS Calculated: 136. MS Found: 137 (M+H).

Preparation of Compound VIQ

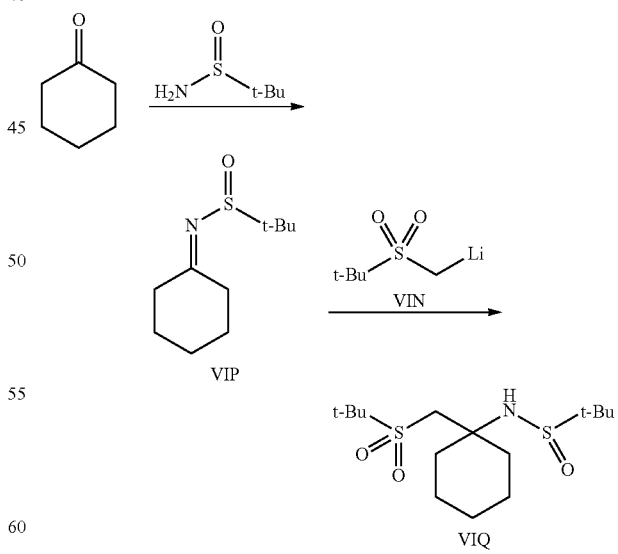

Tert-butyl sulfonamide (24.5 kg, 1.1 eq.) was added to a stirred solution of cyclohexanone (18 kg, 1 eq.) in dry THF (98 L), followed by the addition of TiOEt$_4$ (63 kg, 1.5 eq.), and the reaction was stirred at 60±3° C. for 4 h. The reaction mixture was concentrated by vacuum distillation, maintaining the temperature at 55±3° C. Heptane (54 L) was added to the mixture, and the mixture was concentrated by vacuum distillation, maintaining the temperature at 55±3° C. The heptane charge/distillation was repeated. The resultant mixture containing VIP was cooled, MTBE (36 L) was added and the mixture was maintained at 5±3° C. until used in a later step.

In a separate reactor, compound VIR (37.4 kg, 1.5 eq.) was added with stirring to MTBE (54 L) and the mixture was cooled to 0±3° C. While maintaining a temperature of 2±3° C., butyl lithium (23% in hexane, 76.1 kg, 1.5 eq.) was added over 3 h, and the temperature was maintained for 30 min. Over about 1 h, the solution of VIP in MTBE from the first step was added, keeping the temperature of the mixture at 2±3° C. After 1 h 30 min, MTBE (216 L) was added, keeping the temperature below 25° C., then water was added (27 kg). The temperature was adjusted to 25±3° C. and the mixture was maintained at that temperature for 30 min, after which the titanium salts were removed by centrifugation. The mixture containing VIQ was washed with MTBE (4×36 L) and the filtrate was used immediately in the preparation of VIBb. MS Calculated: 337. MS Found: 338 (M+H).

Preparation of Compound VIBb

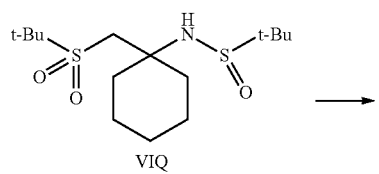

VIQ

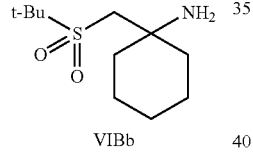

VIBb

Compound VIQ in MTBE (460 kg of solution) was charged to a reactor and with stirring, HCl (50.7 kg, 2.73 eq.) was added while maintaining the temperature below 25° C. Water (112 L) was added and the pH was adjusted to 0.5 to 0.6. The reaction temperature was maintained at 22±3° C. for 1 h and the progress of the reaction was monitored by HPLC. The layers were separated and the aqueous layer was adjusted to pH 12 by adding NaOH (30% aqueous solution approx. 77 kg) while maintaining the temperature at 22±3° C. The reaction temperature was adjusted to 30±3° C. and the mixture kept at that temperature for 15 min. The aqueous solution was extracted with MTBE (2×93 L) and the organic layer containing VIBb was used in the preparation of VIO. MS Calculated: 233. MS Found: 233.

Preparation of Compound VIO

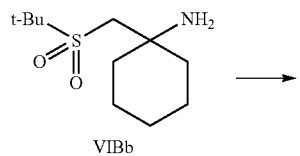

VIBb

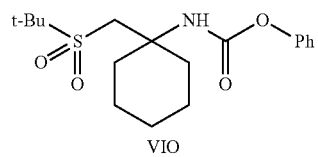

VIO

To a stirred solution of Compound VIBb in MTBE (26.1 kg of VIBb, approx. 205 kg solution) was added DIPEA (15.1 kg, 1.05 eq.) and the temperature was adjusted to 2±3° C. While maintaining that temperature, phenyl chloroformate (18.3 kg, 1.05 eq.) was added and the reaction was held at that temperature for 1 h.

In a separate reactor, water (107 L) was cooled to 2±3° C., and the MTBE solution was added, with stirring, while maintaining the temperature; the reactor containing the MTBE solution was rinsed with MTBE (52 L), the was rinse added to the water mixture, and kept at that temperature for 1 h. The resultant solid was isolated by centrifugation. The solid was washed with cold MTBE (2×52 L) and dried at 40° C. MS Calculated: 353. MS Found: 354 (M+H).

Preparation of Compound VI (via VIO)

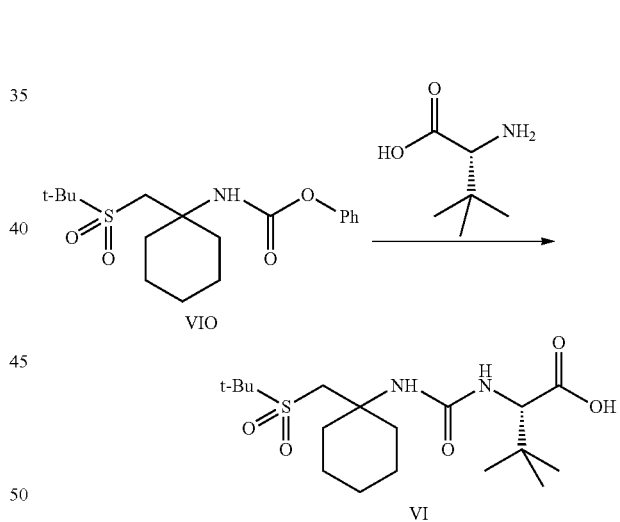

Compound VIO (34.6 kg, 1 eq.) and L-tert-leucine 012.8 kg, 1 eq.) were added to stirred isopropanol and the mixture was heated to 70±3° C. Over about 30 min, tetramethyl guanidine (12.5 kg, 1.1 eq.) was added while maintaining the temperature at 70±3° C. After 1 h, the mixture was cooled to 60±3° C. Water (237 L) was added and the mixture was cooled to 22±3° C. Maintaining the temperature, the pH was adjusted to ≤1.5 with HCl (13 L). Once crystallization began, the mixture was cooled to 2±3° C. and maintained at that temperature for 1 h. The solids were isolated by centrifugation, washed with water (2×35 L) and dried at 50° C. A 94% yield of compound VI was achieved.

We claim:
1. A process for preparing the compound of Formula I

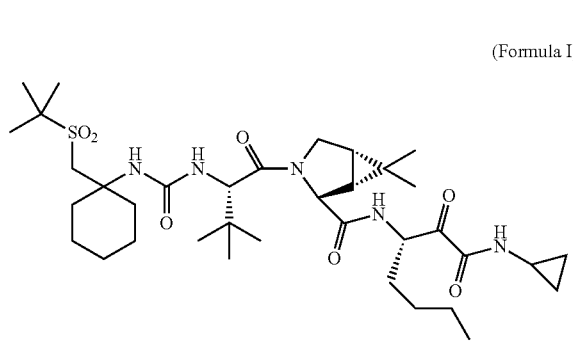

(Formula I)

comprising:
1) coupling a bicyclo intermediate of Formula II with an amine intermediate of Formula III in the presence of coupling reagents to obtain the intermediate alcohol of Formula IV:

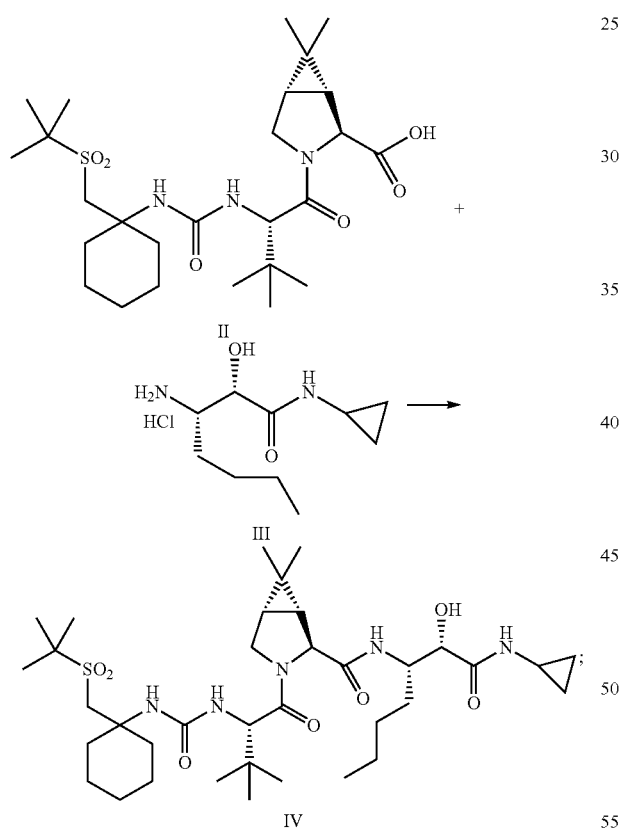

and
2) oxidizing the intermediate of Formula IV.

2. The process of claim 1 wherein the compounds of Formula II and III are coupled using 1-ethyl-3-(3-dimethylaminopropyl)-carbodiimide and 1-hydroxybenzotriazole in the presence of N,N-diisopropylethylamine.

3. The process of claim 1 wherein the compound of Formula IV is oxidized with sodium hypochlorite in the presence of a catalytic or stoichiometric amount of 2,2,6,6-tetramethyl-1-piperidinyloxy free radical.

4. A process for preparing the compound of Formula I

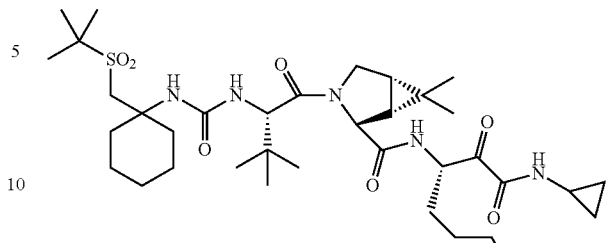

I comprising:
1) coupling the acid of Formula VI with the secondary amine of Formula VII-1 in a water soluble solvent the presence of coupling agents to obtain the compound of Formula Va:

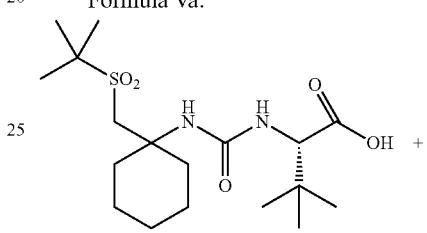

VI

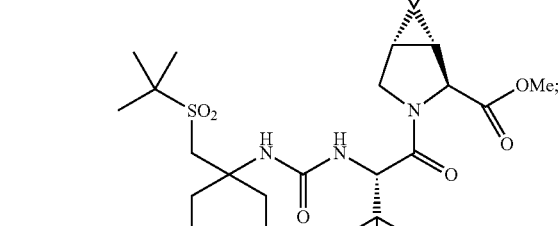

VII-1

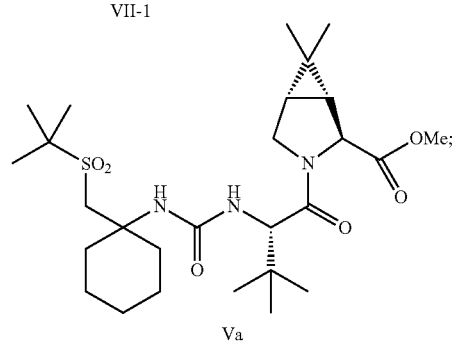

Va 2) converting the methyl ester of Formula Va to the acid of Formula II:

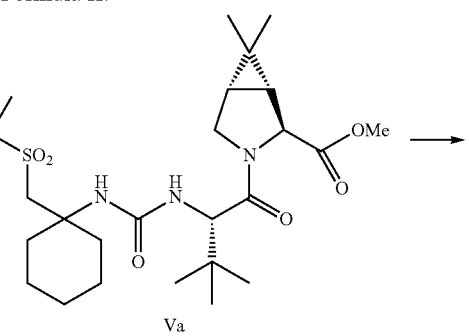

Va

-continued

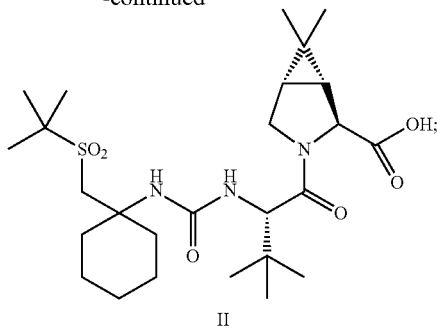

II 3) coupling the acid of Formula II with an amine intermediate of Formula III in the presence of coupling reagents to obtain the intermediate alcohol of Formula IV:

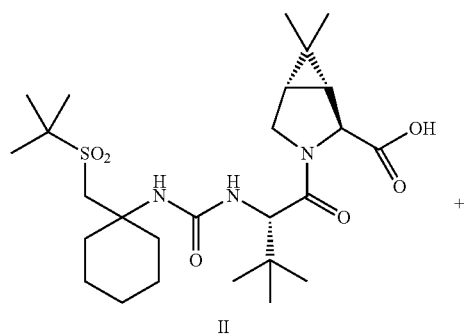

II

+

-continued

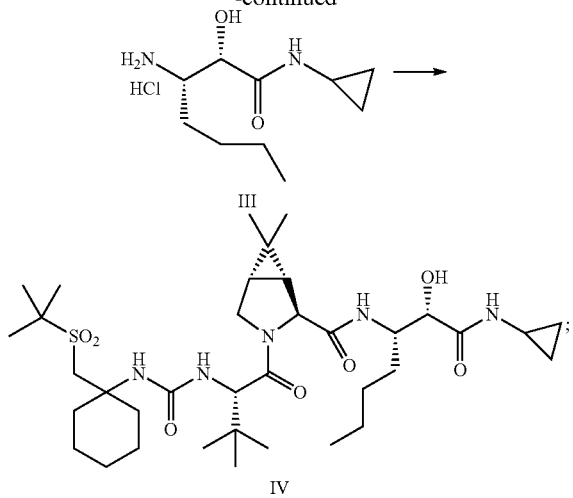

and 4) oxidizing the intermediate of Formula IV.

5. The process of claim 4 wherein the compounds of Formula VI and VII are coupled using 1-ethyl-3-(3-dimethylaminopropyl)-carbodiimide and 1-hydroxybenzotriazole in the presence of N-methylmorpholine in acetonitrile.

6. The process of claim 4 wherein the compounds of Formula II and III are coupled using 1-ethyl-3-(3-dimethylaminopropyl)-carbodiimide and 1-hydroxybenzotriazole in the presence of N,N-diisopropylethylamine.

7. The process of claim 4 wherein the compound of Formula IV is oxidized with sodium hypochlorite in the presence of a catalytic or stoichiometric amount of 2,2,6,6-tetramethyl-1-piperidinyloxy free radical.

* * * * *

UNITED STATES PATENT AND TRADEMARK OFFICE
CERTIFICATE OF CORRECTION

PATENT NO.       : 8,680,294 B2
APPLICATION NO.  : 13/387619
DATED            : March 25, 2014
INVENTOR(S)      : Traverse et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 12 days.

Signed and Sealed this

Twenty-ninth Day of September, 2015

Michelle K. Lee
*Director of the United States Patent and Trademark Office*